US008338414B2

(12) United States Patent
Haruta et al.

(10) Patent No.: US 8,338,414 B2
(45) Date of Patent: *Dec. 25, 2012

(54) IMMUNOSUPPRESSIVE AGENT AND ANTI-TUMOR AGENT COMPRISING HETEROCYCLIC COMPOUND AS ACTIVE INGREDIENT

(75) Inventors: Kazuhiko Haruta, Tokyo (JP); Shinichi Yaguchi, Tokyo (JP); Toshiyuki Matsuno, Tokyo (JP); Yoshio Tsuchida, Tokyo (JP); Tetsuo Watanabe, Tokyo (JP); Kimitomo Yoshioka, Tokyo (JP); Ryogo Yui, Tokyo (JP)

(73) Assignee: Zenyaku Kogyo KabushikiKaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/785,683

(22) Filed: May 24, 2010

(65) Prior Publication Data
US 2010/0267700 A1 Oct. 21, 2010

Related U.S. Application Data

(60) Division of application No. 11/847,593, filed on Aug. 30, 2007, now Pat. No. 7,750,001, which is a continuation of application No. PCT/JP2006/304937, filed on Mar. 13, 2006.

(30) Foreign Application Priority Data

Mar. 11, 2005 (JP) ................................. 2005-069255

(51) Int. Cl.
*A61K 31/535* (2006.01)
*A61K 31/44* (2006.01)
*A61K 31/55* (2006.01)
*C07D 413/14* (2006.01)
*A61P 35/04* (2006.01)
*A01N 43/40* (2006.01)
*A01N 43/62* (2006.01)

(52) U.S. Cl. ....... 514/234.5; 544/83; 544/112; 544/114; 544/358; 514/218; 514/232.5

(58) Field of Classification Search ........................ None
See application file for complete search history.

(56) References Cited

U.S. PATENT DOCUMENTS

| 5,489,591 | A | 2/1996 | Kobayashi et al. |
| 5,656,643 | A | 8/1997 | Spada et al. |
| 5,852,019 | A | 12/1998 | Ejima et al. |
| 6,251,900 | B1 | 6/2001 | Kawashima et al. |
| 7,071,189 | B2 | 7/2006 | Kawashima et al. |
| 7,153,853 | B2 | 12/2006 | Kawashima et al. |
| 2004/0116421 | A1 | 6/2004 | Kawashima et al. |
| 2004/0121996 | A1 | 6/2004 | Barvian et al. |
| 2006/0205742 | A1 | 9/2006 | Kawashina et al. |
| 2006/0247232 | A1 | 11/2006 | Kawashima et al. |
| 2007/0244110 | A1 | 10/2007 | Yaguchi et al. |

FOREIGN PATENT DOCUMENTS

| AU | 2003/272972 | 5/2004 |
| EP | 0 293 078 A1 | 11/1988 |
| EP | 0 640 599 A1 | 3/1995 |
| EP | 0 784 055 A1 | 7/1997 |
| EP | 1020462 | 7/2000 |
| EP | 1389617 | 2/2004 |
| JP | 6-507643 | 9/1994 |
| JP | 9-48776 | 12/1997 |
| WO | 93/17009 | 9/1993 |
| WO | 96/10024 | 4/1996 |
| WO | 99/05138 | 2/1999 |
| WO | 00/43385 | 7/2000 |
| WO | 01/91699 | 12/2001 |
| WO | 01/91699 A2 | 12/2001 |
| WO | 02/088112 A1 | 11/2002 |
| WO | 2004/032930 A1 | 4/2004 |
| WO | 2004/037812 | 5/2004 |
| WO | 2005/095389 | 10/2005 |

OTHER PUBLICATIONS

Patani et al.(Chem. Rev., 1996, 96(8), 3147-3176).*
S. Yaguchi, et al., 96th Annual Meeting of the AACR, Anaheim, CA, USA, Apr. 16-20, 2005, #1691.
Office Action issued Oct. 28, 2010 in Taiwan Patent Application No. 95108509, filed Mar. 13, 2006 (with English-lanugage translation).
Office Action issued Jul. 2, 2010, in Australia Patent Application No. 2006221285, filed Mar. 13, 2006.
Russian web site (Entsikiopedia lekarstv. RLC-Patsient online. RLC-Patsient 2001-glava 2.11 "Sredstve, vilyautshie na immunnuyu sistemu", http://www.risnet,ru/book_RisPatient2001. htm?Partid=91 (with English translation of main portion.
S. Uddin, et al., "Inhibition of phosphatidylinositol 3<'>-kinase induces preferentially killing of PTEN-null T leukemias through AKT pathway", Biochemical and Biophysical, Research Communications, Academic Press Inc., Orlando, FL, US., vol. 320, No. 3, pp. 932-938, XP004518040 ISSN:0006-291X abstract (Jul. 30, 2004).
H-G. Zhang, et al., "Regulation of Tumor Necrosis Factor α-Mediated Apoptosis of Rheumatoid Arthritis Synovia Fibroblasts by the Protein Kinase AKT", Arthritis & Rheumatism, vol. 44, No. 7, pp. 1555-1567 (Jul. 2001).
"Autoimmune Diseases" from the Health Central Network: http://www.healthscout.com/ency/68/487/main.html (printed Feb. 2, 2009).
S. Yaguchi, et al., Molecular Targets and Cancer Therapeutics, Nov. 14-18, 2005 Novel Anticancer Drug Candidate Targeted Phosphatidylinositol-3 Kinase: (2) Vivo Antitumer Efficacy and its molecular Mechanisum, Abstracts published as a Supplement to Clinical Cancer Ressearch, vol. 11, Iss. 23 (Dec. 1, 2005).

(Continued)

*Primary Examiner* — Bong-Sook Baek
(74) *Attorney, Agent, or Firm* — Oblon, Spivak, McClelland, Maier & Neustadt, L.L.P.

(57) ABSTRACT

A novel method for immunosuppressive in a mammal suffering from an immune disease, including administering to the mammal a therapeutically effective amount of a heterocyclic compound represented by the general formula (I) (wherein X or other variables are as defined in the specification) or a pharmaceutically acceptable salt thereof is disclosed. A novel heterocyclic compound represented by the general formula (II) (wherein X or other variables are as defined in the specification) or a pharmaceutically acceptable salt thereof is also disclosed.

12 Claims, 7 Drawing Sheets

OTHER PUBLICATIONS

T. Yamori, et al., Moleclar Targets and Cancer Therapeutics, Nov. 14-18, 2005, Novel Anticancer Drug Candicate Targeted at Phosphatidylinositol-3 Kinase: Identification of the Molecular Target Using Compare Analysis, Abstracts published a a Supplemental to Clinical Cancer Research, vol. 11, Iss. 23 (Dec. 1, 2005).

T. Muenster, et al., "Pharmacotherapeutic strategies for disease-modifying antirheumatic drug (DMARD) combinations to treat rheumatoid arthirits (RA)", Virginia Mason Research Centre, Clin Exp Rheumatol, vol. 17, (Suppl. 18), pp. S29-S36 (1999).

R. Wetzker, et al., "Phosphoinositide 3-Kinases as Targets for Therapeutic Intervention", Current Pharmaceutical Design, vol. 10, pp. 1915-1922 (2004).

A.C. Donahue, et al., "Proliferation and Survival of Activated B Cells Requires Sustained Antigen Receptor Engagement- and Phospholnositide 3-Kinase Activation", The Journal of Immunology, vol. 170, pp. 5851-5860 (2003).

S.G. Ward, et al., "Inhibition of CD28-mediated T cell costimulation by the phosphoinositide 3-kinase inhibitor", Eur. J. Immunol., vol. 25, pp. 526-532 (1995).

P. Workman, "Inhibiting the Phosphoinositide 3-kinase pathway for cancer treatment", Biochemical Society Transactions, vol. 32, Part 2, pp. 393-396 (2004).

S. Uddin, et al., "Inhibition of Phosphatidylinositol 3'-Kinase induces preferentially Killing of PTEN-null T leukemias through AKT pathway", Biochemical and Biophysical Research Communication, vol. 320, pp. 932-938 (2004).

T. Miyashita, et al., "Akt is an endogenous inhibitor toward tumor necrosis factor-related apoptosis inducing ligand-mediated apoptosis in rheumatoid synovial cells", Biochemical and Biophysical Research Communications, vol. 312, pp. 397-404 (2003).

Huang, et al., Cancer Biology & Therapy, vol. 2, No. 3, pp. 222-232 (2003).

T. Matsuno, et al., "Synthesis and Antitumor Activity of Benzimidazolyl-1,3,5-triazine and Benzimidazolylpyrimidine Derivatives" Chem. Pharm. Bull., vol. 48, No. 11, pp. 1778-1781 (Nov. 2000).

Indian Office Action issued Jan. 30, 2012 in Patent Application No. 3220/KOLNP/2007.

Wei Duan et al., "An Anti-Inflammatory Role for a Phosphoinositide 3-kinase Inhibitor LY294002 in a Mouse Asthma Model", International Immunopharmacology, vol. 5, No. 3, Mar. 1, 2005, pp. 495-502.

Mariarosaria Bucci et al., "Endothelial Nitric Oxide Synthase Activation is Critical for Vascular Leakage During Acute Inflammation in Vivo", Proceedings of the National Academy of Sciences of the United States of America, vol. 102, No. 3, Jan. 18, 2005, pp. 904-908.

* cited by examiner

Antibody +

Compound 4   1 μM

Antibody +

Compound 20   1 μM

Antibody +

Compound 24   1 μM

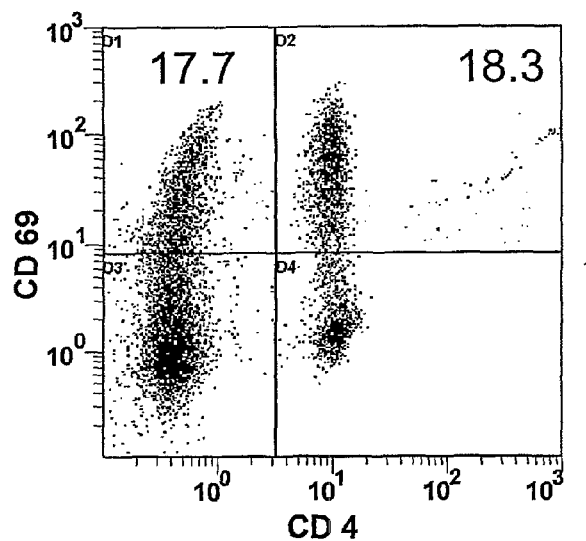
FIG. 1D
Antibody +
Compound 4   1 μM
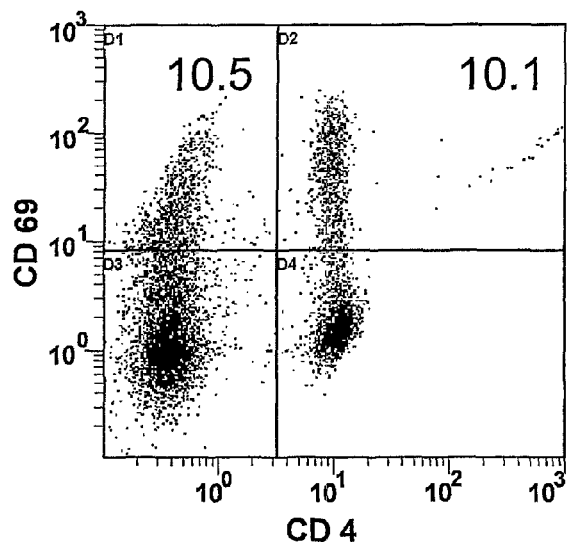
Antibody +
Compound 20   1 μM
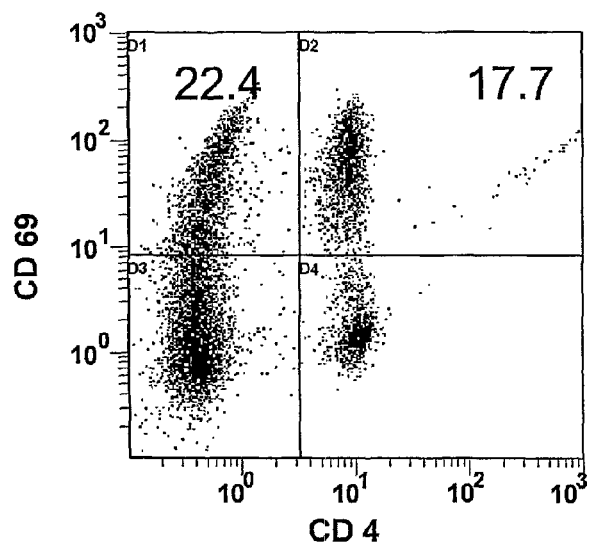
Antibody +
Compound 24   1 μM

IMMUNOSUPPRESSIVE AGENT AND ANTI-TUMOR AGENT COMPRISING HETEROCYCLIC COMPOUND AS ACTIVE INGREDIENT

CROSS-REFERENCE TO RELATED APPLICATIONS

This is a divisional application of U.S. application Ser. No. 11/847,593, filed Aug. 30, 2007, which is a continuation—application under 35 U.S.C. §111(a) and 37 CFR §1.53(b) based on the International Application PCT/JP2006/304937, entitled "IMMUNOSUPPRESSIVE AGENT AND ANTI-TUMOR AGENT COMPRISING HETEROCYCLIC COMPOUND AS ACTIVE INGREDIENT" filed Mar. 13, 2006, which was filed claiming priority to Japanese Patent Application No. 2005-069255 filed Mar. 11, 2005, all of which are hereby incorporated by reference in their entirety.

TECHNICAL FIELD

The present invention relates to novel immunosuppressive agents, and more specifically immunosuppressive agents comprising heterocyclic compounds of a specific structure as effective ingredients. The present invention also relates to novel chemical compounds among the above heterocyclic compounds, and further to the use of such novel compounds as antitumor agents.

BACKGROUND ART

In general, as disorders for which immunosuppressive agents may be used, mention may be made of a number of autoimmune diseases such as rejection after transplantation of organs or tissues, graft versus host disease after bone-marrow transplantation, inflammatory bowel diseases such as ulcerative colitis or Crohn disease, inflammatory or allergenic skin diseases such as psoriasis or atopic dermatitis, inflammatory or allergenic respiratory disorders such as chronic obstructive pulmonary disease or asthma, rheumatoid arthritis, systemic lupus erythematosus, scleroderma, Sjögren syndrome, or the like. In addition, immunosuppressive agents such as cyclophosphamide or methotrexate are employed also in the treatment of hematologic neoplasms such as multiple myeloma, malignant lymphoma, leukemia or the like. Furthermore, immunosuppressive agents may also be employed in combination with antibiotics in the case of the treatment of disorders characterized by an enhanced immune function associated with infection such as sepsis (Non-Patent Document 1).

Thus, a number of immunosuppressive agents are presently utilized as therapeutic agents for the above-mentioned disorders in clinical practice. However, as it now stands, there still remain many problems to be improved due to a failure to obtain a sufficient therapeutic effect and an unexpected occurrence of side effects.

A variety of cells such as T, B lymphocytes and factors are known to be involved in the inducement of the immune response. Since cyclosporin and tacrolimus, which are presently used for organ transplantation or the like, are restricted in their efficacy to T cells, there is a need for immunosuppressive agents which serve as agents for acting on more extensive immune mechanisms, with less side effects in clinical applications, and acting simultaneously on a variety of cells involved in the disorders.

Here, "a variety of cells involved in the disorders" are not limited to immune cells, i.e., T cells, B cells, monocytes, macrophages, NK cells, NKT cells, dendritic cells, neutrophils, basophils, eosinophils, mast cells or the like. They should include cells in which functions are affected by humoral factors released from immune cells or membrane receptors on the immune cells. Examples of these cells include, but are not limited to platelets, vascular endothelial cells, synoviocytes, osteoclasts, osteoblasts, chondrocytes, tracheal epithelial cells, or the like. In addition, in the case where the humoral factors are autoantibodies, cells expressing target antigens are also included.

Regarding benzimidazole ring-substituted s-triazine [1,3,5-triazine] derivatives and pyrimidine derivatives, the present inventors have studied their cytostatic activity on solid tumors, and have performed synthesis of a great number of such compounds as well as verification of the relationship between antitumor activity and chemical structure (see Patent Documents 1, 2, 3, 4 and 5).

In particular, s-triazine derivatives and pyrimidine derivatives having a specific substituent at position 2 of the benzimidazole ring were found to exhibit an enhanced cytostatic activity on solid tumors (see Patent Documents 3, 4 and 5). The processes for the production of such derivatives are described in these patent documents, but are not limited to these, and various reactions such as alkylation, alkylcarbonylation or the like may be induced in the final products to employ the resultant as final compounds.

Non-Patent Document 1: T. Munster et. al. Clin. Exp. Rheumatol., 17 (Suppl. 18): S29-S36 (1999);
Patent Document 1: WO 99/05138 pamphlet
Patent Document 2: WO 00/43385 pamphlet
Patent Document 3: WO 02/088112 pamphlet
Patent Document 4: WO 2004/037812 pamphlet
Patent Document 5: WO 2005/095389 pamphlet

Problems to be Solved by the Invention

The present inventors demonstrated that the above compounds specifically inhibited phosphatidylinositol 3-kinase (PI3K) activity (Non-Patent Document 2). PI3K is an enzyme that phosphorylates phosphatidylinositol (PI) on the cell membrane, classified into three subfamilies according to structures and its substrate specificity. Among these, the compounds of the present invention specifically inhibit class I PI3K. Class I PI3K phosphorylates PI, phosphatidylinositol 4-phosphate, and phosphatidylinositol 4,5-biphosphate to produce phosphatidylinositol 3-phosphate, phosphatidylinositol 3,4-biphosphate, and phosphatidylinositol 3,4,5-triphosphate, respectively. Phosphatidylinositol 3,4,5-triphosphate thus produced serves as an intracellular second messenger. Class I PI3K is expressed in various cells, and exhibits a wide spectrum of functions such as cell proliferation, cell survival, glucose transport, cytoskeleton regulation and the like. In PI3K gene-knockout animals, development of B cells, T cells or the like and signal transduction are obstructed. Furthermore, the degranulation of mast cells and migration of leukocytes are also obstructed (Non-Patent Document 3).

It is known that B cell proliferation by lipopolysaccharides (LPS) or anti-IgM antibodies is inhibited by wortmannin or LY294002, PI3K inhibitors (Non-Patent Document 4). Furthermore, wortmannin inhibits T cell proliferation induced by anti-CD3 antibodies and anti-CD28 antibodies (Non-Patent Document 5).

Hematologic neoplasms are characterized by a spontaneous enhancement of cell division and an inhibition of apoptosis of the immune cells. However, abnormalities of PI3K cascades such as reduction of PTEN proteins that dephosphorylate phosphatidylinositol 3,4,5-triphosphate and enhancement of Akt phosphorylation have been reported (Non-Patent Document 6). Furthermore, it was demonstrated that the inhibition of PI3K may result in the inhibition of the cell division and the induction of apoptosis of various hematologic neoplasms (e.g., Non-Patent Document 7).

Rheumatoid arthritis is a disorder characterized by immune abnormalities and hypertrophy of synovial tissues. It is known that the hypertrophy of synovial tissues results from proliferation and inhibition of apoptosis of synoviocytes. In inflamed synovial tissues of patients with rheumatoid arthritis, the levels of phosphorylated Akt were increased due to the activation of PI3K (Non-Patent Document 8). Moreover, it was revealed that proliferation and inhibition of apoptosis of synoviocytes were normalized by the inhibition of PI3K in vitro study (Non-Patent Document 9).

However, wortmannin and LY294002 have not been put to clinical use due to their toxicity. Furthermore, although a lot of candidates that have therapeutic potential for a wide spectrum of disorders such as inflammations, cancers and others have been developed to take advantage of PI3K's inhibitory property, none has been put to clinical use. Thus, there is a need for immunosuppressive agents which normalize the hyperfunctioning of PI3K in various cells involved in disorder of immune system without exhibiting any toxicity to living subjects.

Non-Patent Document 2: S. Yaguchi et al., 96th Annual Meeting of the AACR, Anaheim, Calif., USA. Apr. 16-20, 2005, #1691.

Non-Patent Document 3: R. Wetzker and C. Rommel, Current Pharmaceutical Design, 2004, 10, 1915-1922

Non-Patent Document 4: A. C. Donahue and D. A. Fruman, J. Immunol. 2003, 170, 5851-5860

Non-Patent Document 5: S. G. Ward et al., Eur J. Immunol. 1995, 25, 526-532

Non-Patent Document 6: P. Workmann, Biochem. Soc. Trans. 2004, 32, 393-396

Non-Patent Document 7: S. Uddin et al., Biochem. Biophys. Res. Commun. 2004, 320, 932-938

Non-Patent Document 8: H. Zhang et al., Arthritis Rheum 2001, 44, 1555-1567

Non-Patent Document 9: T. Miyashita et al., Biochem Biophys Res Commun 2003, 312, 397-404

Means to Solve the Problems

In view of the foregoing, the present inventors have conducted extensive research on the heterocyclic compounds disclosed in Patent Documents 1, 2, 3, 4 and 5 on the assumption that some might be useful for the disorders for which immunosuppressive agents are used, such as for autoimmune diseases, organ transplantation, allergic diseases, hematologic neoplasm, sepsis or the like. As a result, they found that the heterocyclic compounds represented by the following general formula (I) are effective, arriving at completion of the present invention.

Thus, one aspect of the present invention provides an immunosuppressive agent comprising as an effective ingredient a heterocyclic compound represented by the general Formula (I):

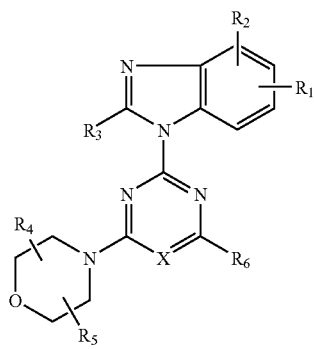

wherein,

X represents a nitrogen atom or CH;

both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl or a hydroxymethyl group;

$R_4$ and $R_5$ represent a hydrogen atom, or a $C_1$-$C_6$ alkyl group;

$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);

or a pharmaceutically acceptable salt thereof.

Here, one embodiment provides an immunosuppressive agent wherein in Formula (I), either of $R_1$ or $R_2$ is a hydroxyl group. Another embodiment provides an immunosuppressive agent wherein in Formula (I), either of $R_1$ or $R_2$ is a hydroxyl group, and $R_3$ is a difluoromethyl. A further embodiment provides an immunosuppressive agent wherein in Formula (I), both of $R_1$ and $R_2$ are hydrogens, and $R_3$ is a difluoromethyl. A further embodiment provides an immunosuppressive agent wherein in Formula (I), $R_6$ is a 4-acetylpiperazine.

In the foregoing, the disorders to be treated may be rejection and graft versus host diseases, inflammatory bowel diseases such as ulcerative colitis or Crohn disease, inflammatory or allergenic skin diseases such as psoriasis or atopic dermatitis; inflammatory or allergenic respiratory disorders such as obstructive pulmonary diseases or asthma; autoimmune diseases such as rheumatoid arthritis, systemic lupus erythematosus, scleroderma or Sjögren syndrome; hematological neoplasms such as malignant lymphoma, multiple myeloma, chronic leukemia, acute leukemia, or myelocytic leukemia; sepsis, fulminant hepatitis and the like.

Here, one embodiment provides a PI3K inhibitor wherein in Formula (I), either of $R_1$ or $R_2$ is a hydroxyl group. Another embodiment provides a PI3K inhibitor wherein in Formula (I), either of $R_1$ or $R_2$ is a hydroxyl group, and $R_3$ is a difluoromethyl. A further embodiment provides a PI3K inhibitor wherein in Formula (I), both of $R_1$ and $R_2$ are hydrogens, and $R_3$ is a difluoromethyl. Furthermore, a PI3K inhibitor wherein in Formula (I), $R_6$ is a 4-acetylpiperazine is provided.

In the foregoing, the disorders to be treated may be rejection and graft versus host diseases, inflammatory bowel diseases such as ulcerative colitis or Crohn disease, inflammatory or allergenic skin diseases such as psoriasis or atopic dermatitis; inflammatory or allergenic respiratory disorders such as obstructive pulmonary diseases or asthma; autoimmune diseases such as rheumatoid arthritis, systemic lupus erythematosus, scleroderma or Sjögren syndrome; hematological neoplasms such as malignant lymphoma, multiple myeloma, chronic leukemia, or acute leukemia; sepsis, fulminant hepatitis and the like.

Among the heterocyclic compounds of Formula (I) which are used in the immunosuppressive agents in accordance with the present invention, some compounds are novel in their structures. Thus, in another aspect, the present invention provides a heterocyclic compound represented by the general Formula (II):

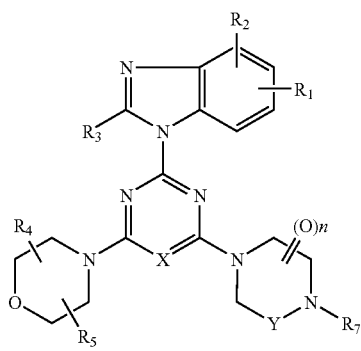

wherein,
n represents 0-2;
X represents a nitrogen atom or CH;
Y represents —$(CH_2)n_1$-, wherein $n_i$ is 1-2;
$R_1$ and $R_2$, both or either, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a hydrogen atom, a difluoromethyl group, an amino group, a $C_1$-$C_6$ alkylamino group, a methyl or a hydroxymethyl group;
$R_4$ and $R_5$ represent a hydrogen atom, or a $C_1$-$C_6$ alkyl group;
$R_7$ represents a hydrogen atom, a $C_1$-$C_6$ alkyl group, a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, or a substituted carbamoyl;
or a pharmaceutically acceptable salt thereof.

For example, the compounds according to the Formula (II) may be as follows:
4-(4-acetylpiperazin-1-yl)-2-(2-difluoromethylbenzimidazol-1-yl)-6-morpholino-1,3,5-triazine;
4-(4-acetylpiperazin-1-yl)-2-(2-difluoromethylbenzimidazol-1-yl)-6-(cis-2,3-dimethylmorpholino)-1,3,5-triazine;
4-(4-acetylpiperazin-1-yl)-2-(2-difluoromethylbenzimidazol-1-yl)-6-(trans-2,3-dimethylmorpholino)-1,3,5-triazine;
4-(4-acetylpiperazin-1-yl)-2-(2-difluoromethylbenzimidazol-1-yl)-6-(2,2-dimethylmorpholino)-1,3,5-triazine;
4-(4-acetylpiperazin-1-yl)-2-(2-difluoromethyl-4-hydroxybenzimidazol-1-yl)-6-morpholino-1,3,5-triazine;
4-(4-acetylpiperazin-1-yl)-2-(4-amino-2-difluoromethylbenzimidazol-1-yl)-6-morpholino-1,3,5-triazine;
4-(4-acetylpiperazin-1-yl)-2-(2-hydroxymethylbenzimidazol-1-yl)-6-morpholino-1,3,5-triazine;
4-(4-acetylpiperazin-1-yl)-2-(2-difluoromethylbenzimidazol-1-yl)-6-morpholinopyrimidine;
4-(4-acetylpiperazin-1-yl)-2-(2-difluoromethylbenzimidazol-1-yl)-6-(cis-2,3-dimethylmorpholino)pyrimidine;
4-(4-acetylpiperazin-1-yl)-2-(2-difluoromethylbenzimidazol-1-yl)-6-(trans-2,3-dimethylmorpholino)pyrimidine;
4-(4-acetylpiperazin-1-yl)-2-(2-difluoromethylbenzimidazol-1-yl)-6-(2,2-dimethylmorpholino)pyrimidine;
4-(4-acetylpiperazin-1-yl)-2-(2-difluoromethyl-4-hydroxybenzimidazol-1-yl)-6-morpholinopyrimidine;
4-(4-acetylpiperazin-1-yl)-2-(4-amino-2-difluoromethylbenzimidazol-1-yl)-6-morpholinopyrimidine;
4-(4-acetylpiperazin-1-yl)-2-(2-hydroxymethylbenzimidazol-1-yl)-6-morpholinopyrimidine;
2-(2-difluoromethylbenzimidazol-1-yl)-4-[4-(N,N-dimethylcarbamoyl)piperazin-1-yl]-6-morpholino-1,3,5-triazine;
2-(2-difluoromethylbenzimidazol-1-yl)-4-[4-(N,N-dimethylcarbamoyl)piperazin-1-yl]-6-(cis-2,3-dimethylmorpholino)-1,3,5-triazine;
2-(2-difluoromethylbenzimidazol-1-yl)-4-[4-(N,N-dimethylcarbamoyl)piperazin-1-yl]-6-(trans-2,3-dimethylmorpholino)-1,3,5-triazine;
2-(2-difluoromethylbenzimidazol-1-yl)-4-[4-(N,N-dimethylcarbamoyl)piperazin-1-yl]-6-(2,2-dimethylmorpholino)-1,3,5-triazine;
2-(2-difluoromethyl-4-hydroxybenzimidazol-1-yl)-4-[4-(N,N-dimethylcarbamoyl)piperazin-1-yl]-6-morpholino-1,3,5-triazine;
2-(4-amino-2-difluoromethylbenzimidazol-1-yl)-4-[4-(N,N-dimethylcarbamoyl)piperazin-1-yl]-6-morpholino-1,3,5-triazine;
2-(2-hydroxymethylbenzimidazol-1-yl)-4-[4-(N,N-dimethylcarbamoyl)piperazin-1-yl]-6-morpholino-1,3,5-triazine;
2-(2-difluoromethylbenzimidazol-1-yl)-4-[4-(N,N-dimethylcarbamoyl)piperazin-1-yl]-6-morpholinopyrimidine;
2-(2-difluoromethylbenzimidazol-1-yl)-4-[4-(N,N-dimethylcarbamoyl)piperazin-1-yl]-6-(cis-2,3-dimethylmorpholino)pyrimidine;
2-(2-difluoromethylbenzimidazol-1-yl)-4-[4-(N,N-dimethylcarbamoyl)piperazin-1-yl]-6-(trans-2,3-dimethylmorpholino)pyrimidine;
2-(2-difluoromethylbenzimidazol-1-yl)-4-[4-(N,N-dimethylcarbamoyl)piperazin-1-yl]-6-(2,2-dimethylmorpholino)pyrimidine;
2-(2-difluoromethyl-4-hydroxybenzimidazol-1-yl)-4-[4-(N,N-dimethylcarbamoyl)piperazin-1-yl]-6-morpholinopyrimidine;
2-(4-amino-2-difluoromethylbenzimidazol-1-yl)-4-[4-(N,N-dimethylcarbamoyl)piperazin-1-yl]-6-morpholinopyrimidine;
2-(2-hydroxymethylbenzimidazol-1-yl)-4-[4-(N,N-dimethylcarbamoyl)piperazin-1-yl]-6-morpholinopyrimidine;
2-(2-difluoromethylbenzimidazol-1-yl)-4-[4-(2-furoyl)piperazin-1-yl]-6-morpholino-1,3,5-triazine;
2-(2-difluoromethylbenzimidazol-1-yl)-4-[4-(2-furoyl)piperazin-1-yl]-6-(cis-2,3-dimethylmorpholino)-1,3,5-triazine;

2-(2-difluoromethylbenzimidazol-1-yl)-4-[4-(2-furoyl)piperazin-1-yl]-6-(trans-2,3-dimethylmorpholino)-1,3,5-triazine;

2-(2-difluoromethylbenzimidazol-1-yl)-4-[4-(2-furoyl)piperazin-1-yl]-6-(2,2-dimethylmorpholino)-1,3,5-triazine;

2-(2-difluoromethyl-4-hydroxybenzimidazol-1-yl)-4-[4-(2-furoyl)piperazin-1-yl]-6-morpholino-1,3,5-triazine;

2-(4-amino-2-difluoromethylbenzimidazol-1-yl)-4-[4-(2-furoyl)piperazin-1-yl]-6-morpholino-1,3,5-triazine;

4-[4-(2-furoyl)piperazin-1-yl]-2-(2-hydroxymethylbenzimidazol-1-yl)-6-morpholino-1,3,5-triazine;

2-(2-difluoromethylbenzimidazol-1-yl)-4-[4-(2-furoyl)piperazin-1-yl]-6-morpholinopyrimidine;

2-(2-difluoromethylbenzimidazol-1-yl)-4-[4-(2-furoyl)piperazin-1-yl]-6-(cis-2,3-dimethylmorpholino)pyrimidine;

2-(2-difluoromethylbenzimidazol-1-yl)-4-[4-(2-furoyl)piperazin-1-yl]-6-(trans-2,3-dimethylmorpholino)pyrimidine;

2-(2-difluoromethylbenzimidazol-1-yl)-4-[4-(2-furoyl)piperazin-1-yl]-6-(2,2-dimethylmorpholino)pyrimidine;

2-(2-difluoromethyl-4-hydroxybenzimidazol-1-yl)-4-[4-(2-furoyl)piperazin-1-yl]-6-morpholinopyrimidine;

2-(4-amino-2-difluoromethylbenzimidazol-1-yl)-4-[4-(2-furoyl)piperazin-1-yl]-6-morpholinopyrimidine;

4-[4-(2-furoyl)piperazin-1-yl]-2-(2-hydroxymethylbenzimidazol-1-yl)-6-morpholinopyrimidine;

4-(4-acetonylpiperazin-1-yl)-2-(2-difluoromethylbenzimidazol-1-yl)-6-morpholino-1,3,5-triazine;

4-(4-acetonylpiperazin-1-yl)-2-(2-difluoromethylbenzimidazol-1-yl)-6-(cis-2,3-dimethylmorpholino)-1,3,5-triazine;

4-(4-acetonylpiperazin-1-yl)-2-(2-difluoromethylbenzimidazol-1-yl)-6-(trans-2,3-dimethylmorpholino)-1,3,5-triazine;

4-(4-acetonylpiperazin-1-yl)-2-(2-difluoromethylbenzimidazol-1-yl)-6-(2,2-dimethylmorpholino)-1,3,5-triazine;

4-(4-acetonylpiperazin-1-yl)-2-(2-difluoromethyl-4-hydroxybenzimidazol-1-yl)-6-morpholino-1,3,5-triazine;

4-(4-acetonylpiperazin-1-yl)-2-(4-amino-2-difluoromethylbenzimidazol-1-yl)-6-morpholino-1,3,5-triazine;

4-(4-acetonylpiperazin-1-yl)-2-(2-hydroxymethylbenzimidazol-1-yl)-6-morpholino-1,3,5-triazine;

4-(4-acetonylpiperazin-1-yl)-2-(2-difluoromethylbenzimidazol-1-yl)-6-morpholinopyrimidine;

4-(4-acetonylpiperazin-1-yl)-2-(2-difluoromethylbenzimidazol-1-yl)-6-(cis-2,3-dimethylmorpholino)pyrimidine;

4-(4-acetonylpiperazin-1-yl)-2-(2-difluoromethylbenzimidazol-1-yl)-6-(trans-2,3-dimethylmorpholino)pyrimidine;

4-(4-acetonylpiperazin-1-yl)-2-(2-difluoromethylbenzimidazol-1-yl)-6-(2,2-dimethylmorpholino)pyrimidine;

4-(4-acetonylpiperazin-1-yl)-2-(2-difluoromethyl-4-hydroxybenzimidazol-1-yl)-6-morpholinopyrimidine;

4-(4-acetonylpiperazin-1-yl)-2-(4-amino-2-difluoromethylbenzimidazol-1-yl)-6-morpholinopyrimidine;

4-(4-acetonylpiperazin-1-yl)-2-(2-hydroxymethylbenzimidazol-1-yl)-6-morpholinopyrimidine;

2-(2-difluoromethylbenzimidazol-1-yl)-4-morpholino-6-(4-propionylpiperazin-1-yl)-1,3,5-triazine;

2-(2-difluoromethylbenzimidazol-1-yl)-4-(cis-2,3-dimethylmorpholino)-6-(4-propionylpiperazin-1-yl)-1,3,5-triazine;

2-(2-difluoromethylbenzimidazol-1-yl)-4-(trans-2,3-dimethylmorpholino)-6-(4-propionylpiperazin-1-yl)-1,3,5-triazine;

2-(2-difluoromethylbenzimidazol-1-yl)-4-(2,2-dimethylmorpholino)-6-(4-propionylpiperazin-1-yl)-1,3,5-triazine;

2-(2-difluoromethyl-4-hydroxybenzimidazol-1-yl)-4-morpholino-6-(4-propionylpiperazin-1-yl)-1,3,5-triazine;

2-(4-amino-2-difluoromethylbenzimidazol-1-yl)-4-morpholino-6-(4-propionylpiperazin-1-yl)-1,3,5-triazine;

2-(2-hydroxymethylbenzimidazol-1-yl)-4-morpholino-6-(4-propionylpiperazin-1-yl)-1,3,5-triazine;

2-(2-difluoromethylbenzimidazol-1-yl)-4-morpholino-6-(4-propionylpiperazin-1-yl)pyrimidine;

2-(2-difluoromethylbenzimidazol-1-yl)-4-(cis-2,3-dimethylmorpholino)-6-(4-propionylpiperazin-1-yl)pyrimidine;

2-(2-difluoromethylbenzimidazol-1-yl)-4-(trans-2,3-dimethylmorpholino)-6-(4-propionylpiperazin-1-yl)pyrimidine;

2-(2-difluoromethylbenzimidazol-1-yl)-4-(2,2-dimethylmorpholino)-6-(4-propionylpiperazin-1-yl)pyrimidine;

2-(2-difluoromethyl-4-hydroxybenzimidazol-1-yl)-4-morpholino-6-(4-propionylpiperazin-1-yl)pyrimidine;

2-(4-amino-2-difluoromethylbenzimidazol-1-yl)-4-morpholino-6-(4-propionylpiperazin-1-yl)pyrimidine;

2-(2-hydroxymethylbenzimidazol-1-yl)-4-morpholino-6-(4-propionylpiperazin-1-yl)pyrimidine;

2-(2-difluoromethylbenzimidazol-1-yl)-4-(4-methoxyacetylpiperazin-1-yl)-6-morpholino-1,3,5-triazine;

2-(2-difluoromethylbenzimidazol-1-yl)-4-(4-methoxyacetylpiperazin-1-yl)-6-(cis-2,3-dimethylmorpholino)-1,3,5-triazine;

2-(2-difluoromethylbenzimidazol-1-yl)-4-(4-methoxyacetylpiperazin-1-yl)-6-(trans-2,3-dimethylmorpholino)-1,3,5-triazine;

2-(2-difluoromethylbenzimidazol-1-yl)-4-(4-methoxyacetylpiperazin-1-yl)-6-(2,2-dimethylmorpholino)-1,3,5-triazine;

2-(2-difluoromethyl-4-hydroxybenzimidazol-1-yl)-4-(4-methoxyacetylpiperazin-1-yl)-6-morpholino-1,3,5-triazine;

2-(4-amino-2-difluoromethylbenzimidazol-1-yl)-4-(4-methoxyacetylpiperazin-1-yl)-6-morpholino-1,3,5-triazine;

2-(2-hydroxymethylbenzimidazol-1-yl)-4-(4-methoxyacetylpiperazin-1-yl)-6-morpholino-1,3,5-triazine;

2-(2-difluoromethylbenzimidazol-1-yl)-4-(4-methoxyacetylpiperazin-1-yl)-6-morpholinopyrimidine;

2-(2-difluoromethylbenzimidazol-1-yl)-4-(4-methoxyacetylpiperazin-1-yl)-6-(cis-2,3-dimethylmorpholino)pyrimidine;

2-(2-difluoromethylbenzimidazol-1-yl)-4-(4-methoxyacetylpiperazin-1-yl)-6-(trans-2,3-dimethylmorpholino)pyrimidine;

2-(2-difluoromethylbenzimidazol-1-yl)-4-(4-methoxyacetylpiperazin-1-yl)-6-(2,2-dimethylmorpholino)pyrimidine;

2-(2-difluoromethyl-4-hydroxybenzimidazol-1-yl)-4-(4-methoxyacetylpiperazin-1-yl)-6-morpholinopyrimidine;

2-(4-amino-2-difluoromethylbenzimidazol-1-yl)-4-(4-methoxyacetylpiperazin-1-yl)-6-morpholinopyrimidine;

2-(2-hydroxymethylbenzimidazol-1-yl)-4-(4-methoxyacetylpiperazin-1-yl)-6-morpholinopyrimidine;

2-(2-difluoromethylbenzimidazol-1-yl)-4-[4-(3-hydroxypropyl)piperazin-1-yl]-6-morpholino-1,3,5-triazine;

2-(2-difluoromethylbenzimidazol-1-yl)-4-[4-(3-hydroxypropyl)piperazin-1-yl]-6-(cis-2,3-dimethylmorpholino)-1,3,5-triazine;

2-(2-difluoromethylbenzimidazol-1-yl)-4-[4-(3-hydroxypropyl)piperazin-1-yl]-6-(trans-2,3-dimethylmorpholino)-1,3,5-triazine;

2-(2-difluoromethylbenzimidazol-1-yl)-4-[4-(3-hydroxypropyl)piperazin-1-yl]-6-(2,2-dimethylmorpholino)-1,3,5-triazine;
2-(2-difluoromethyl-4-hydroxybenzimidazol-1-yl)-4-[4-(3-hydroxypropyl)piperazin-1-yl]-6-morpholino-1,3,5-triazine;
2-(4-amino-2-difluoromethylbenzimidazol-1-yl)-4-[4-(3-hydroxypropyl)piperazin-1-yl]-6-morpholino-1,3,5-triazine;
2-(2-hydroxymethylbenzimidazol-1-yl)-4-[4-(3-hydroxypropyl)piperazin-1-yl]-6-morpholino-1,3,5-triazine;
2-(2-difluoromethylbenzimidazol-1-yl)-4-[4-(3-hydroxypropyl)piperazin-1-yl]-6-morpholinopyrimidine;
2-(2-difluoromethylbenzimidazol-1-yl)-4-[4-(3-hydroxypropyl)piperazin-1-yl]-6-(cis-2,3-dimethylmorpholino)pyrimidine;
2-(2-difluoromethylbenzimidazol-1-yl)-4-[4-(3-hydroxypropyl)piperazin-1-yl]-6-(trans-2,3-dimethylmorpholino)pyrimidine;
2-(2-difluoromethylbenzimidazol-1-yl)-4-[4-(3-hydroxypropyl)piperazin-1-yl]-6-(2,2-dimethylmorpholino)pyrimidine;
2-(2-difluoromethyl-4-hydroxybenzimidazol-1-yl)-4-[4-(3-hydroxypropyl)piperazin-1-yl]-6-morpholinopyrimidine;
2-(4-amino-2-difluoromethylbenzimidazol-1-yl)-4-[4-(3-hydroxypropyl)piperazin-1-yl]-6-morpholinopyrimidine;
2-(2-hydroxymethylbenzimidazol-1-yl)-4-[4-(3-hydroxypropyl)piperazin-1-yl]-6-morpholinopyrimidine;
2-(2-difluoromethylbenzimidazol-1-yl)-4-(4-methoxycarbonylpiperazin-1-yl)-6-morpholino-1,3,5-triazine;
2-(2-difluoromethylbenzimidazol-1-yl)-4-(4-methoxycarbonylpiperazin-1-yl)-6-(cis-2,3-dimethylmorpholino)-1,3,5-triazine;
2-(2-difluoromethylbenzimidazol-1-yl)-4-(4-methoxycarbonylpiperazin-1-yl)-6-(trans-2,3-dimethylmorpholino)-1,3,5-triazine;
2-(2-difluoromethylbenzimidazol-1-yl)-4-(4-methoxycarbonylpiperazin-1-yl)-6-(2,2-dimethylmorpholino)-1,3,5-triazine;
2-(2-difluoromethyl-4-hydroxybenzimidazol-1-yl)-4-(4-methoxycarbonylpiperazin-1-yl)-6-morpholino-1,3,5-triazine;
2-(4-amino-2-difluoromethylbenzimidazol-1-yl)-4-(4-methoxycarbonylpiperazin-1-yl)-6-morpholino-1,3,5-triazine;
2-(2-hydroxymethylbenzimidazol-1-yl)-4-(4-methoxycarbonylpiperazin-1-yl)-6-morpholino-1,3,5-triazine;
2-(2-difluoromethylbenzimidazol-1-yl)-4-(4-methoxycarbonylpiperazin-1-yl)-6-morpholinopyrimidine;
2-(2-difluoromethylbenzimidazol-1-yl)-4-(4-methoxycarbonylpiperazin-1-yl)-6-(cis-2,3-dimethylmorpholino)pyrimidine;
2-(2-difluoromethylbenzimidazol-1-yl)-4-(4-methoxycarbonylpiperazin-1-yl)-6-(trans-2,3-dimethylmorpholino)pyrimidine;
2-(2-difluoromethylbenzimidazol-1-yl)-4-(4-methoxycarbonylpiperazin-1-yl)-6-(2,2-dimethylmorpholino)pyrimidine;
2-(2-difluoromethyl-4-hydroxybenzimidazol-1-yl)-4-(4-methoxycarbonylpiperazin-1-yl)-6-morpholinopyrimidine;
2-(4-amino-2-difluoromethylbenzimidazol-1-yl)-4-(4-methoxycarbonylpiperazin-1-yl)-6-morpholinopyrimidine;
2-(2-hydroxymethylbenzimidazol-1-yl)-4-(4-methoxycarbonylpiperazin-1-yl)-6-morpholinopyrimidine;
2-(2-difluoromethylbenzimidazol-1-yl)-4-morpholino-6-(5-oxo-1,4-diazepan-1-yl)-1,3,5-triazine;
2-(2-difluoromethylbenzimidazol-1-yl)-4-morpholino-6-(3-oxopiperazin-1-yl)-1,3,5-triazine; and
2-(2-difluoromethylbenzimidazol-1-yl)-6-(3,5-dioxopiperazin-1-yl)-4-morpholino-1,3,5-triazine.

Furthermore, the present inventors have found novel uses as antitumor agents for the novel compounds represented by the above Formula (II). Thus, a further embodiment relates to an antitumor agent comprising a compound of Formula (II) as an effective ingredient. The disorders of interest may include, but are not limited to, lung cancer, prostate cancer, breast cancer, colon cancer, gastric cancer, pancreatic cancer, liver cancer, esophageal cancer, brain tumor, ovarian cancer, uterine cancer, malignant melanoma, renal cancer, head and neck cancer, skin cancer, bladder cancer, osteogenic sarcoma, biliary tract cancer, vulvar cancer, testicular neoplasm, penile cancer, colorectal cancer, mediastinal neoplasm, urothelial carcinoma, choriocarcinoma, soft tissue sarcoma, thyroid cancer, parathyroid cancer, adrenal cancer, malignant pheochromocytoma, germ cell tumor and the like.

Furthermore, the present invention relates to the following various embodiments. The present invention relates to a method for immunosuppression comprising administering to a mammal a therapeutically effective amount of a heterocyclic compound represented by the general Formula (I):

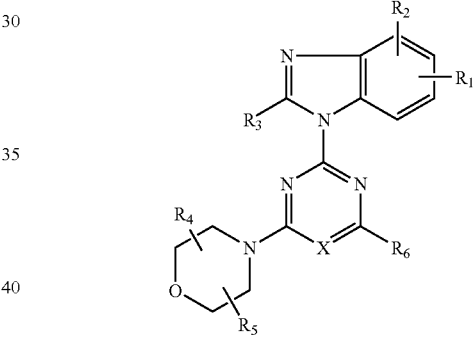

wherein,
X represents a nitrogen atom or CH;
both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a hydrogen atom, a difluoromethyl group, an amino group, a $C_1$-$C_6$ alkylamino group, a methyl or a hydroxymethyl group;
$R_4$ and $R_5$ represent a hydrogen atom, or a $C_1$-$C_6$ alkyl group;
$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);

or a pharmaceutically acceptable salt thereof.

Here, in one embodiment, in Formula (I), either of $R_1$ or $R_2$ is hydroxyl group. In Another embodiment, in Formula (I), either of $R_1$ or $R_2$ is hydroxyl group, and $R_3$ is difluoromethyl. In a further embodiment, in Formula (I), both of $R_1$ and $R_2$ are hydrogens, and $R_3$ is difluoromethyl. In a further embodiment, in Formula (I), $R_6$ is 4-acetylpiperazine.

Furthermore, as the disorders to be treated, mention can be made of rejection and graft versus host disease; inflammatory bowel diseases such as ulcerative colitis or Crohn disease; inflammatory or allergenic skin diseases such as psoriasis or atopic dermatitis; inflammatory or allergenic respiratory disorders such as obstructive pulmonary diseases or asthma; autoimmune diseases such as rheumatoid arthritis, systemic lupus erythematosus, scleroderma, Sjögren syndrome, or the like; hematologic neoplasms such as malignant lymphoma, multiple myeloma, chronic leukemia, acute leukemia or the like; sepsis, fulminant hepatitis and the like.

Yet another embodiment relates to a method for treating tumors comprising administering to a patient a therapeutically effective amount of a heterocyclic compound represented by the general Formula (II):

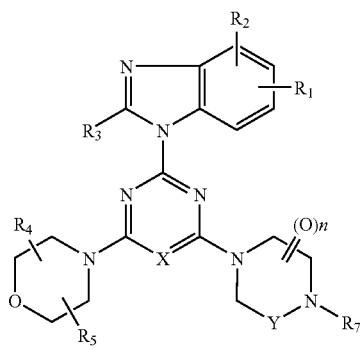

wherein, n represents 0-2;

X represents a nitrogen atom or CH;

Y represents —$(CH_2)n_1$-, wherein $n_1$ is 1-2;

$R_1$ and $R_2$, both or either, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl or a hydroxymethyl group;

$R_4$ and $R_5$ represent a hydrogen atom, or a $C_1$-$C_6$ alkyl group;

$R_7$ represents a hydrogen atom, a $C_1$-$C_6$ alkyl group, a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, or a substituted carbamoyl;

or a pharmaceutically acceptable salt thereof.

In yet another embodiment, the present invention relates to an immunosuppressive composition comprising a therapeutically effective amount of a heterocyclic compound represented by the general Formula (II):

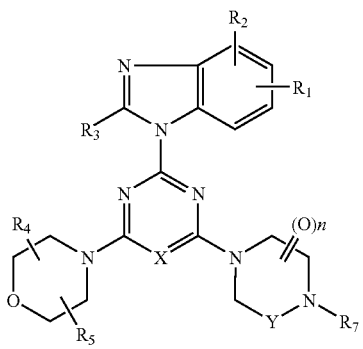

wherein, n represents 0-2;

X represents a nitrogen atom or CH;

Y represents —$(CH_2)n_1$-, wherein $n_1$ is 1-2;

$R_1$ and $R_2$, both or either, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl or a hydroxymethyl group;

$R_4$ and $R_5$ represent a hydrogen atom, or a $C_1$-$C_6$ alkyl group;

$R_7$ represents a hydrogen atom, a $C_1$-$C_6$ alkyl group, a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, or a substituted carbamoyl; or a pharmaceutically acceptable salt thereof and a pharmaceutically acceptable carrier. In a yet further embodiment, the invention relates to a composition, in particular a pharmaceutical composition, and more preferably an antitumor composition, comprising a therapeutically effective amount of a heterocyclic compound represented by the general Formula (II) or a pharmaceutically acceptable salt thereof and a pharmaceutically acceptable carrier.

Furthermore, the present invention relates to the following various embodiments. The present invention relates to a PI3K inhibition method comprising administering to a mammal a therapeutically effective amount of a heterocyclic compound represented by the general Formula (I):

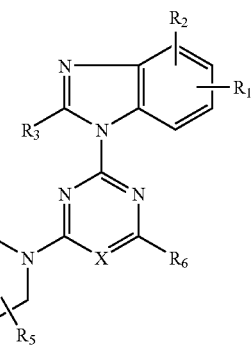

wherein,

X represents a nitrogen atom or CH;

both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl or a hydroxymethyl group;

$R_4$ and $R_5$ represent a hydrogen atom, or a $C_1$-$C_6$ alkyl group;

$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);

or a pharmaceutically acceptable salt thereof.

Here, in one embodiment, in Formula (I), either of $R_1$ or $R_2$ is hydroxyl group. In another embodiment, in Formula (I), either of $R_1$ or $R_2$ is hydroxyl group, and $R_3$ is difluoromethyl. In a further embodiment, in Formula (I), both of $R_1$ and $R_2$ are hydrogens, and $R_3$ is difluoromethyl. In a further embodiment, in Formula (I), $R_6$ is 4-acetylpiperazine.

Furthermore, as the disorders to be treated, mention can be made of rejection and graft versus host disease; inflammatory bowel diseases such as ulcerative colitis or Crohn disease; inflammatory or allergenic skin diseases such as psoriasis or atopic dermatitis; inflammatory or allergenic respiratory disorders such as obstructive pulmonary diseases or asthma; autoimmune diseases such as rheumatoid arthritis, systemic lupus erythematosus, scleroderma, Sjögren syndrome, or the like; hematologic neoplasms such as malignant lymphoma, multiple myeloma, chronic leukemia, acute leukemia or the like; sepsis, fulminant hepatitis and the like.

In yet another embodiment, the present invention relates to a PI3K inhibitory composition comprising a therapeutically effective amount of a heterocyclic compound represented by Formula (I):

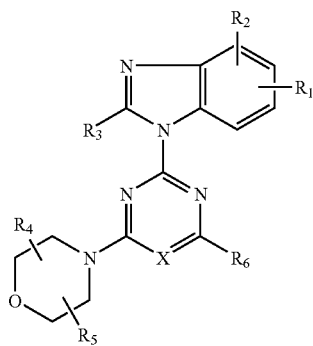

wherein,

X represents a nitrogen atom or CH;

both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl or a hydroxymethyl group;

$R_4$ and $R_5$ represent a hydrogen atom, or a $C_1$-$C_6$ alkyl group;

$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);

or a pharmaceutically acceptable salt thereof and a pharmaceutically acceptable carrier. In a yet further embodiment, the invention relates to a composition, in particular a pharmaceutical composition, and more preferably a PI3K inhibitory composition, comprising a therapeutically effective amount of a heterocyclic compound represented by the general Formula (II) or a pharmaceutically acceptable salt thereof and a pharmaceutically acceptable carrier.

Furthermore, the present invention relates to use of a heterocyclic compound represented by Formula (I):

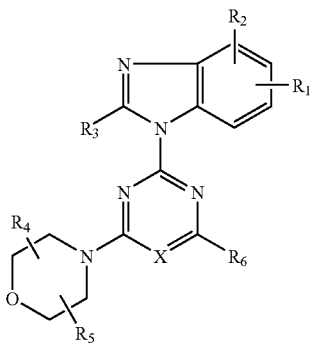

wherein,

X represents a nitrogen atom or CH;

both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;

$R_3$ represents a hydrogen atom, a difluoromethyl group, an amino group, a $C_1$-$C_6$ alkylamino group, a methyl or a hydroxymethyl group;

$R_4$ and $R_5$ represent a hydrogen atom, or a $C_1$-$C_6$ alkyl group;

$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);

or a pharmaceutically acceptable salt thereof in the manufacture of a medicament for the treatment of immune diseases, or as an immunosuppressive agent.

Here, in one embodiment, in Formula (I), either of $R_1$ or $R_2$ is hydroxyl group. In another embodiment, in Formula (I), either of $R_1$ or $R_2$ is hydroxyl group, and $R_3$ is difluoromethyl. In a further embodiment, in Formula (I), both of $R_1$ and $R_2$ are hydrogens, and $R_3$ is difluoromethyl. In a further embodiment, in Formula (I), $R_6$ is a 4-acetylpiperazine.

Furthermore, as the disorders to be treated, mention can be made of rejection and graft versus host disease; inflammatory bowel diseases such as ulcerative colitis or Crohn disease; inflammatory or allergenic skin diseases such as psoriasis or atopic dermatitis; inflammatory or allergenic respiratory disorders such as obstructive pulmonary diseases or asthma; autoimmune diseases such as rheumatoid arthritis, systemic lupus erythematosus, scleroderma, Sjögren syndrome, or the like; hematologic neoplasms such as malignant lymphoma, multiple myeloma, chronic leukemia, acute leukemia or the like; sepsis, fulminant hepatitis and the like.

In yet another embodiment, the present invention relates to use of a heterocyclic compound represented by the general Formula (II):

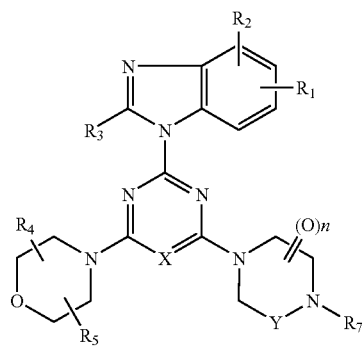

wherein,
n represents 0-2;
X represents a nitrogen atom or CH;
Y represents —$(CH_2)n_1$-, wherein $n_1$ is 1-2;
$R_1$ and $R_2$, both or either, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a hydrogen atom, a difluoromethyl group, an amino group, a $C_1$-$C_6$ alkylamino group, a methyl or a hydroxymethyl group;
$R_4$ and $R_5$ represent a hydrogen atom, or a $C_1$-$C_6$ alkyl group;
$R_7$ represents a hydrogen atom, a $C_1$-$C_6$ alkyl group, a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, or a substituted carbamoyl;
or a pharmaceutically acceptable salt thereof in the manufacture of a composition for treatment of tumors.

In yet another embodiment, the present invention relates to use of a heterocyclic compound represented by Formula (I):

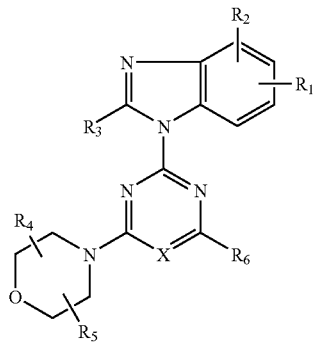

wherein,
X represents a nitrogen atom or CH;
both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a hydrogen atom, a difluoromethyl group, an amino group, a $C_1$-$C_6$ alkylamino group, a methyl or a hydroxymethyl group;
$R_4$ and $R_5$ represent a hydrogen atom, or a $C_1$-$C_6$ alkyl group;
$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);
or a pharmaceutically acceptable salt thereof in the manufacture of a medicament for the inhibition of PI3K or as a PI3K inhibition agent.

Here, in one embodiment, in Formula (I), either of $R_1$ or $R_2$ is hydroxyl group. In another embodiment, in Formula (I), either of $R_1$ or $R_2$ is hydroxyl group, and $R_3$ is difluoromethyl. In a further embodiment, in Formula (I), both of $R_1$ and $R_2$ are hydrogens, and $R_3$ is difluoromethyl. In a further embodiment, in Formula (I), $R_6$ is a 4-acetylpiperazine.

Furthermore, as the disorders to be treated, mention can be made of rejection and graft versus host disease; inflammatory bowel diseases such as ulcerative colitis or Crohn disease; inflammatory or allergenic skin diseases such as psoriasis or atopic dermatitis; inflammatory or allergenic respiratory disorders such as obstructive pulmonary diseases or asthma; autoimmune diseases such as rheumatoid arthritis, systemic lupus erythematosus, scleroderma, Sjögren syndrome, or the like; hematologic neoplasms such as malignant lymphoma, multiple myeloma, chronic leukemia, acute leukemia or the like; sepsis, fulminant hepatitis and the like.

Yet other embodiments, modes and features of the present invention will be apparent to those skilled in the art in view of the detailed description below.

Effect of the Invention

The agents of the invention are effective for the prevention or treatment of the disorders attributable to the hyperfunctioning of PI3K such as autoimmune diseases, organ transplantation, allergenic or inflammatory disorders, hematologic neoplasms, sepsis, and treatment of tumors.

BRIEF EXPLANATION OF THE DRAWINGS

[FIGS. 1A, 1B, 1C and 1D] Diagrams showing the effects of test substances on the upregulation of CD 69 expression and CD 40L expression on human peripheral blood mononuclear cells induced by anti-human CD3 antibody and anti-human CD28 antibody.

DESCRIPTION OF THE PREFERRED EMBODIMENTS OF THE INVENTION

Figure 1A:
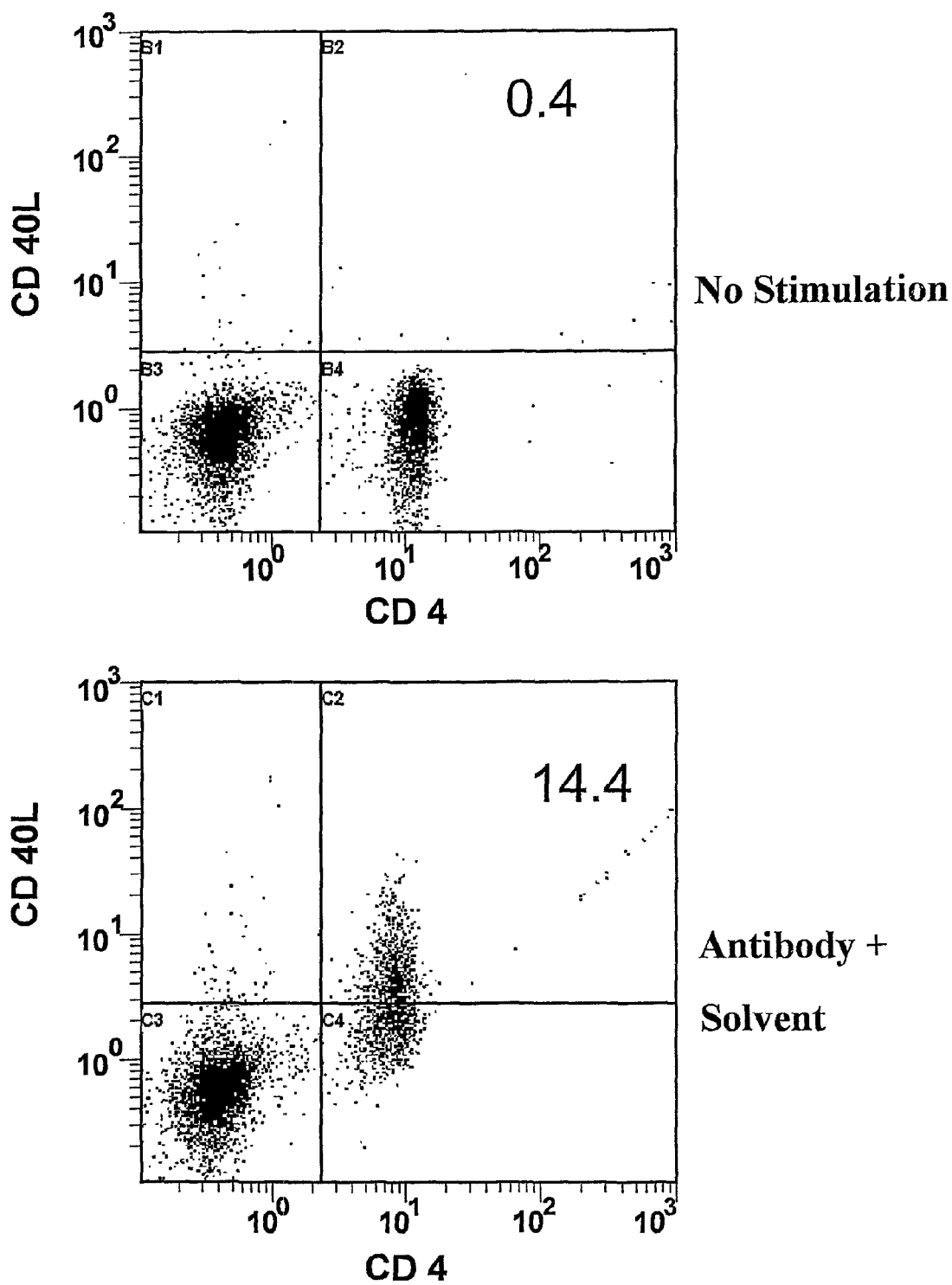
Figure 1B:
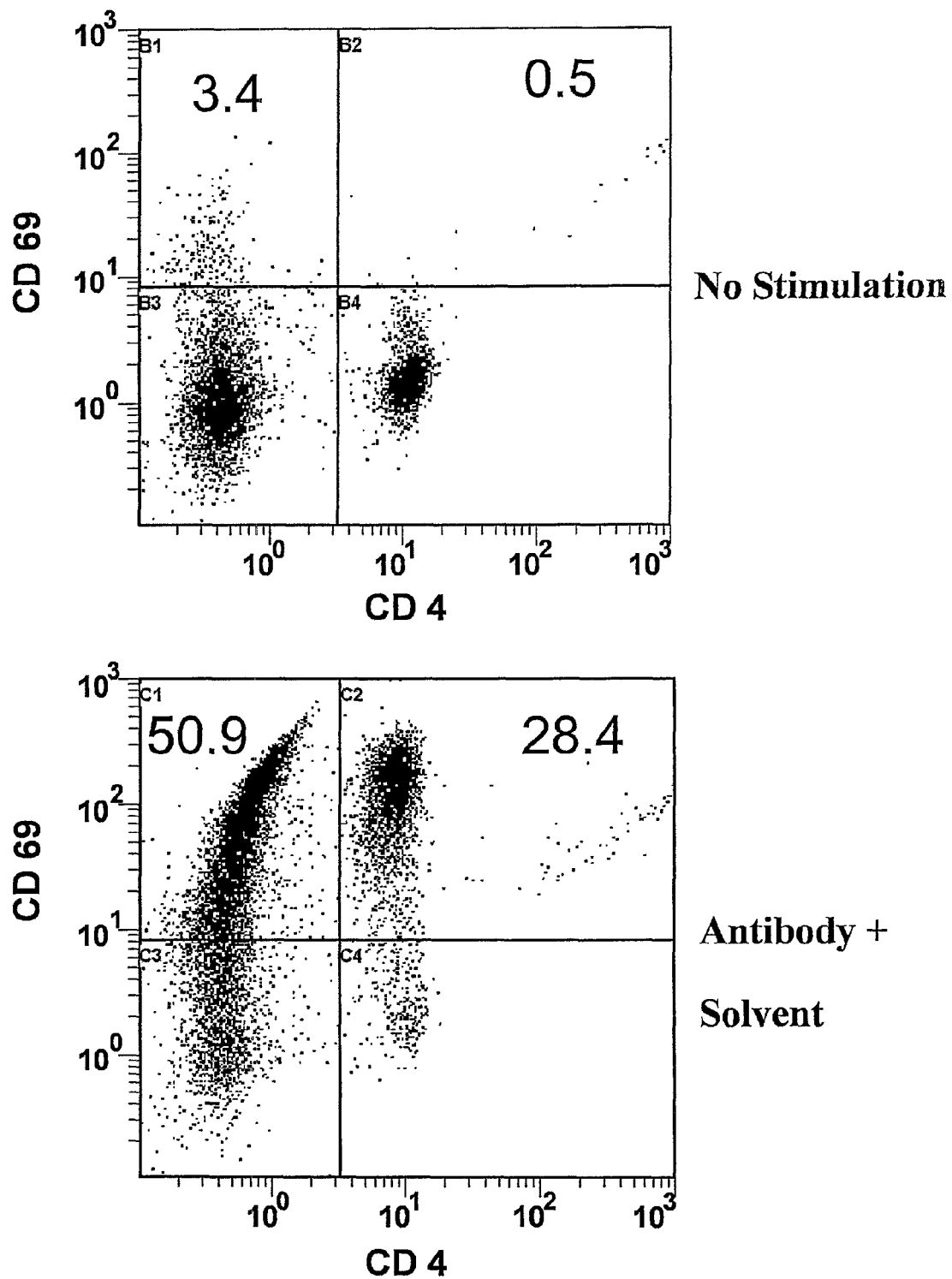
Figure 1C:
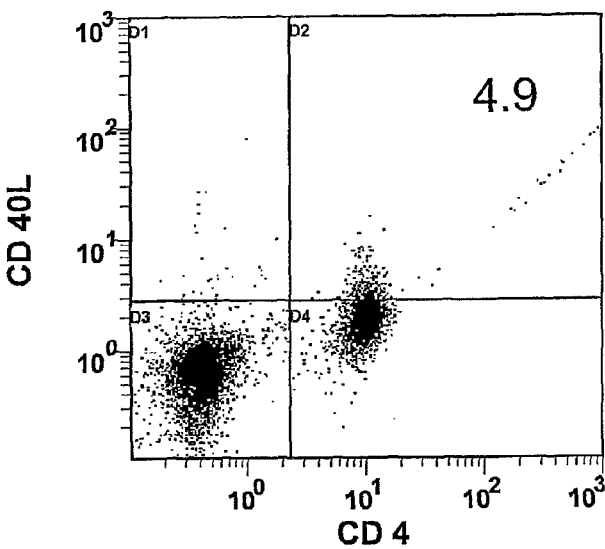
Figure 1C:
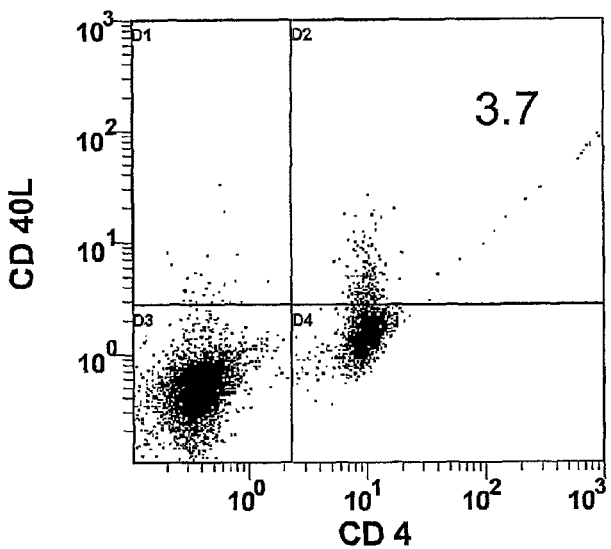
Figure 1C:
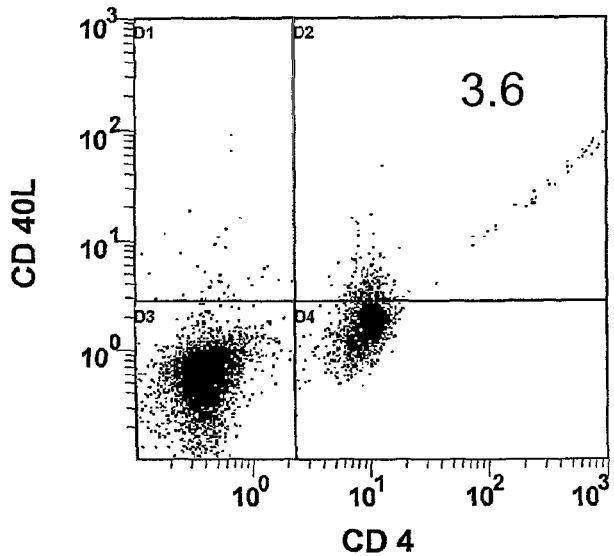

The heterocyclic compound for use in the present invention is the one represented by the general Formula (I):

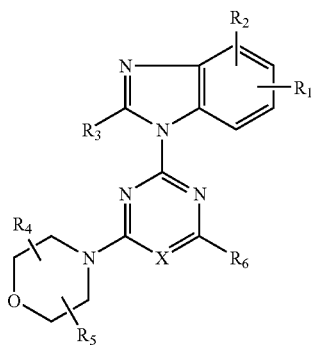

wherein,
X represents a nitrogen atom or CH;
both or either of $R_1$ and $R_2$ represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a hydrogen atom, a difluoromethyl group, an amino group, a $C_1$-$C_6$ alkylamino group, a methyl or a hydroxymethyl group;
$R_4$ and $R_5$ represent a hydrogen atom, or a $C_1$-$C_6$ alkyl group;
$R_6$ represents a morpholino (optionally substituted with one or two $C_1$-$C_6$ alkyl groups), a pyrrolidinyl (optionally substituted with a hydroxy $C_1$-$C_6$ alkyl), a piperidino (which is optionally substituted with one or two oxygen atoms, a hydroxyl group, a formyl, or a $C_1$-$C_6$ alkyl), a piperazinyl (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl), or a 1,4-diazepano (optionally substituted with one or two oxygen atoms, the nitrogen at position 4 being optionally substituted with a substituent selected from the group consisting of a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, and a substituted carbamoyl);
or its pharmaceutically acceptable salt.

In the above formula, "$C_1$-$C_6$" without any limitation means a group having 1 to 6 carbon atoms. "$C_1$-$C_6$ alkyl" includes alkyl groups of linear or branched chain, such as methyl, ethyl, n-propyl, isopropyl, n-butyl, tert-butyl, n-pentyl, n-hexyl and the like. "$C_1$-$C_6$ alkoxy" includes alkoxy groups with linear or branched chain, such as methoxy, ethoxy, n-propoxy, isopropoxy, n-butoxy, tert-butoxy, sec-butoxy, n-pentyloxy, n-hexyloxy and the like. "Hydroxy $C_1$-$C_6$ alkyl" means those groups having a hydroxyl group bonded to any of the carbon atoms of the group defined by the above "$C_1$-$C_6$ alkyl".

When the above heterocyclic compound has an asymmetric carbon atom in its structure, isomers from the asymmetric carbon atom and their mixture (racemic compounds) exist, and any such compounds are to be included among the compounds of the present invention.

Furthermore, the heterocyclic compounds that are used as effective ingredients of the present invention may be in the form of an acid addition salt as a pharmaceutically acceptable salt. Appropriate acid addition salts include inorganic acid salts such as hydrochlorides, sulfates, hydrobromides, nitrates, phosphates or the like, and organic acid salts such as acetates, oxalates, propionates, glycollates, lactates, pyruvates, malonates, succinates, maleates, fumarates, malates, tartrates, citrates, benzoates, cinnamates, methane sulfonates, benzene sulfonates, p-toluene sulfonates, salicylates or the like.

The compounds which can be used as the effective ingredients of the present invention include, but are not limited to, the following heterocyclic compounds:
2-(2-Methylbenzimidazol-1-yl)-4,6-dimorpholino-1,3,5-triazine (Compound 1)
2-(Benzimidazol-1-yl)-4-(trans-2,3-dimethylmorpholino)-6-morpholino-1,3,5-triazine (Compound 2)
4,6-Dimorpholino-2-(2-hydroxymethylbenzimidazol-1-yl)-1,3,5-triazine (Compound 3)
2-(2-Difluoromethylbenzimidazol-1-yl)-4,6-dimorpholino-1,3,5-triazine (Compound 4)
2-(2-Aminobenzimidazol-1-yl)-4,6-dimorpholinopyrimidine (Compound 5)
2-(2-Aminobenzimidazol-1-yl)-4,6-dimorpholino-1,3,5-triazine (Compound 6)
2-(2-Difluoromethylbenzimidazol-1-yl)-4-piperidino-6-morpholino-1,3,5-triazine (Compound 7)
2-(6-Amino-2-difluoromethylbenzimidazol-1-yl)-4-(cis-2,3-dimethylmorpholino)-6-morpholino-1,3,5-triazine (Compound 8)
2-(2-Difluoromethyl-6-ethoxybenzimidazol-1-yl)-4,6-dimorpholino-1,3,5-triazine (Compound 9)
2-(2-Difluoromethyl-4-methylbenzimidazol-1-yl)-4,6-dimorpholino-1,3,5-triazine (Compound 10)
2-(2-Difluoromethyl-4-hydroxybenzimidazol-1-yl)-4-morpholino-6-(2,6-dimethylmorpholino)pyrimidine (Compound 11)

2-(2-Difluoromethyl-5-hydroxybenzimidazol-1-yl)-4,6-dimorpholino-1,3,5-triazine (Compound 12)
2-(6-Amino-2-difluoromethylbenzimidazol-1-yl)-4-(2,2-dimethylmorpholino)-6-morpholino-1,3,5-triazine (Compound 13)
2-(4-Amino-2-difluoromethylbenzimidazol-1-yl)-4,6-dimorpholino-1,3,5-triazine (Compound 14)
2-(2-Difluoromethyl-4-hydroxybenzimidazol-1-yl)-4,6-dimorpholino-1,3,5-triazine (Compound 15)
2-(2-Difluoromethyl-6-hydroxybenzimidazol-1-yl)-4,6-dimorpholino-1,3,5-triazine (Compound 16)
2-(5-Amino-2-difluoromethylbenzimidazol-1-yl)-4,6-di(2,6-dimethylmorpholino)pyrimidine (Compound 17)
2-(2-Difluoromethyl-4-hydroxybenzimidazol-1-yl)-4,6-dimorpholinopyrimidine (Compound 18)
2-(6-Amino-4-chloro-2-difluoromethylbenzimidazol-1-yl)-4-(2,2-dimethylmorpholino)-6-morpholino-1,3,5-triazine (Compound 19)
2-(2-Difluoromethyl-4-hydroxybenzimidazol-1-yl)-4-(2-hydroxymethyl-pyrrolidin-1-yl)-6-morpholino-1,3,5-triazine (Compound 20)
2-(2-Difluoromethyl-4-hydroxybenzimidazol-1-yl)-4-(2,2-dimethylmorpholino)-6-morpholinopyrimidine (Compound 21)
2-(2-Difluoromethyl-4-hydroxybenzimidazol-1-yl)-4-(3,3-dimethylmorpholino)-6-morpholinopyrimidine (Compound 22)
2-(2-Difluoromethyl-5-methoxybenzimidazol-1-yl)-4,6-dimorpholino-1,3,5-triazine (Compound 23)
2-(2-Difluoromethyl-4-methoxybenzimidazol-1-yl)-4-(cis-2,6-dimethyl-morpholino)-6-morpholinopyrimidine (Compound 24)
2-(2-Difluoromethylbenzimidazol-1-yl)-4-morpholino-6-(5-oxo-1,4-diazepan-1-yl)-1,3,5-triazine (Compound 25)
2-(2-Difluoromethylbenzimidazol-1-yl)-4-(4-hydroxypiperizin-1-yl)-6-morpholino-1,3,5-triazine (Compound 26)
2-(2-Difluoromethylbenzimidazol-1-yl)-4-[4-(2-hydroxyethyl)piperazin-1-yl]-6-morpholino-1,3,5-triazine (Compound 27)
4-(4-Acetylpiperazin-1-yl)-2-(2-difluoromethylbenzimidazol-1-yl)-6-morpholino-1,3,5-triazine (Compound 28)
2-(2-Difluoromethylbenzimidazol-1-yl)-4-(4-benzylcarbonylpiperazin-1-yl)-6-morpholino-1,3,5-triazine (Compound 29)
4-(4-Acetonylpiperazin-1-yl)-2-(2-difluoromethylbenzimidazol-1-yl)-6-morpholino-1,3,5-triazine (Compound 30)
2-(2-Difluoromethylbenzimidazol-1-yl)-4-[4-(2-furoyl)piperazin-1-yl]-6-morpholino-1,3,5-triazine (Compound 31)
2-(2-Difluoromethylbenzimidazol-1-yl)-4-[4-(N,N-dimethylcarbamoyl)piperazin-1-yl]-6-morpholino-1,3,5-triazine (Compound 32)
2-(2-Difluoromethylbenzimidazol-1-yl)-4-(4-methoxylacetylpiperazin-1-yl)-6-morpholino-1,3,5-triazine (Compound 33)
2-(2-Difluoromethylbenzimidazol-1-yl)-4-[4-(3-hydroxypropyl)piperazin-1-yl]-6-morpholino-1,3,5-triazine (Compound 34)
2-(2-Difluoromethylbenzimidazol-1-yl)-4-morpholino-6-(4-propionylpiperazin-1-yl)-1,3,5-triazine (Compound 35)
2-(2-Difluoromethyl-4-methoxybenzimidazol-1-yl)-4-(2,2-dimethylmorpholino)-6-morpholinopyrimidine (Compound 36)
2-(2-Difluoromethyl-4-methoxybenzimidazol-1-yl)-4-(cis-2,3-dimethyl-morpholino)-6-morpholinopyrimidine (Compound 37)
2-(2-Difluoromethyl-4-ethoxybenzimidazol-1-yl)-4-(2,2-dimethylmorpholino)-6-morpholinopyrimidine (Compound 38)

As will be demonstrated in Examples to be hereinafter described, the agents of the present invention inhibit the activation of T cells and B cells induced by Con A, LPS, anti-IgM antibody, anti-CD3 antibody+anti-CD28 antibody, thereby exhibiting PI3K inhibitory action on the immune cells. Thus, the drugs of the present invention can be used in the treatment and prevention of disorders of immune system attributable to the hyperfunctioning of PI3K.

As disorders of immune system attributable to the hyperfunctioning of PI3K, mention may be made of: autoimmune diseases such as rheumatoid arthritis, systemic lupus erythematosus, scleroderma, Sjögren syndrome, or the like; organ dysfunction associated with autoimmune diseases such as uveitis, glomerulonephritis, thyroiditis, pancreatitis, bone destruction or the like; rejection after transplantation of tissues, graft versus host disease after bone-marrow transplantation; inflammatory bowel diseases such as ulcerative colitis or Crohn disease; inflammatory or allergenic skin diseases such as psoriasis or atopic dermatitis; inflammatory or allergenic respiratory disorders such as chronic obstructive pulmonary disease or asthma; allergenic conjunctivitis or rhinitis; hematologic neoplasm originated from immune cells, such as B-cell lymphoma, T-cell lymphoma, myeloid leukemia or the like; sepsis triggered by infection with gram-negative bacteria or coronavirus, severe acute respiratory syndrome, fulminant hepatitis or the like.

While the agents of the present invention can be applied to mammals such as humans, dogs, cats, rabbits, hamsters, rats, mice or the like, the administration regimen, formulation and dosage for application to humans will be particularly explained below.

The agents of the present invention may be administered orally or parenterally, and tablets, coated-tablets, powdered drugs, granules, capsules, microcapsules, syrups or the like may be used as the dosage form for oral administration whereas eye drops, inhalants, injectable form (including lyophilizates for injection which are to be dissolved upon application), suppositories, poultices or the like may be used as the dosage form for parenteral administration. The formulation of these dosage forms may be effected using pharmaceutically acceptable excipients, binders, lubricants, disintegrants, suspending agents, emulsifiers, preservatives, stabilizing agents and dispersants, such as lactose, sucrose, starch, dextrin, crystalline cellulose, kaolin, calcium carbonate, talc, magnesium stearate, distilled water or saline.

When used in oral dosage forms, the dosages of the effective ingredient will differ depending on the symptoms, age, weight or the like of the patient, but a daily dose of 10-500 mg may be administered in 2-3 portions for an adult weighing 60 kg. In addition, the dosages will also differ depending on the symptoms of the patient in the case of ophthalmic solutions, inhalation to lungs or the nasal cavity, and injection to inflamed articular cavities, but a daily dose of 1-100 μg may be administered in 2-3 portions for an adult.

EXAMPLES

Production Examples

Some examples of the heterocyclic compounds represented by the general Formula (I) were produced according to the processes disclosed in the examples of Patent Documents 3, 4 and 5, and described below.

The synthesis was preformed with reference to Patent Documents 1-3.

Production Example 1

2-(2-Methylbenzimidazol-1-yl)-4,6-dimorpholino-1,3,5-triazine (Compound 1)

Melting point: 218-20° C. (Decomposed)
NMR (CDCl$_3$) δ: 3.03 (3 H, s), 3.7-3.9 (16H, m), 7.2-7.4 (2H, m), 7.7-7.8 (1H, m), 8.1-8.3 (1H, m)
MS m/z: 381 (M$^+$)

Production Example 2

2-(Benzimidazol-1-yl)-4-(trans-2,3-dimethylmorpholino)-6-morpholino-1,3,5-triazine (Compound 2)

Melting point: 147-150° C.
NMR (CDCl$_3$) δ: 1.1-1.5 (6H, m), 2.7-3.0 (1H, m), 3.4-3.6 (1H, m), 3.7-4.0 (8H, m), 4.1-4.3 (1H, m), 4.4-4.7 (2H, m), 7.3-7.4 (2H, m), 7.7-7.9 (1H, m), 8.3-8.4 (1H, m), 8.98 (1H, s).

Production Example 3

4,6-Dimorpholino-2-(2-hydroxymethylbenzimidazol-1-yl)-1,3,5-triazine (Compound 3)

Melting point: 208-210° C. (Decomposed)
NMR (CDCl$_3$) δ: 3.7-3.9 (16H, m), 4.59 (1H, t, J=6 Hz), 5.15 (2H, d, J=7 Hz), 7.2-7.4 (2H, m), 7.7-7.8 (1H, m), 8.3-8.4 (1H, m)
MS m/z: 397 (M$^+$)

Production Example 4

2-(2-Difluoromethylbenzimidazol-1-yl)-4,6-dimorpholino-1,3,5-triazine (Compound 4)

Melting point: 211-214° C.
NMR (CDCl$_3$) δ: 3.79 (8H, t, J=4 Hz), 3.88 (8H, t, J=4 Hz), 7.3-7.4 (2H, m), 7.56 (1H, t, J=53 Hz), 7.88 (1H, d, J=7 Hz), 8.32 (1H, d, J=7 Hz).
MS m/z: 417 (M$^+$)

Production Example 5

2-(2-Aminobenzimidazol-1-yl)-4,6-dimorpholinopyrimidine (Compound 5)

Melting point: 237-239° C.
NMR (CDCl$_3$) δ: 3.59 (8H, t, J=5 Hz), 3.84 (8H, t, J=5 Hz), 5.46 (1H, s), 6.65 (2H, brs), 7.06 (1H, t, J=7 Hz), 7.18 (1H, t, J=7 Hz), 7.37 (1H, d, J=7 Hz), 8.1 (1H, d, 7 Hz)
MS m/z: 381 (M$^+$)

Production Example 6

2-(2-Aminobenzimidazol-1-yl)-4,6-dimorpholino-1,3,5-triazine (Compound 6)

Melting point: 298-300° C. (Decomposed)
NMR (CDCl$_3$) δ: 3.7-3.9 (16H, m), 6.74 (2H, brs), 7.05 (1H, t, J=7 Hz), 7.20 (1H, t, J=7 Hz), 7.39 (1H, d, J=7 Hz), 8.20 (1H, d, 7 Hz)
MS m/z: 382 (M$^+$)

Production Example 7

2-(2-Difluoromethylbenzimidazol-1-yl)-4-piperidino-6-morpholino-1,3,5-triazine (Compound 7)

Melting point: 190-192° C.
NMR (CDCl$_3$) δ: 1.5-1.8 (6H, m), 3.7-3.9 (12H, m), 7.3-7.5 (2H, m), 7.61 (1H, t, J=54 Hz), 7.90 (1H, d, J=8 Hz), 8.34 (1H, d, 8 Hz)
MS m/z: 415 (M$^+$)

Production Example 8

2-(6-Amino-2-difluoromethylbenzimidazol-1-yl)-4-(cis-2,3-dimethylmorpholino)-6-morpholino-1,3,5-triazine (Compound 8)

Melting point: 220-222° C. (Decomposed)
NMR (CDCl$_3$) δ: 1.22 (3H, d, J=9 Hz), 1.26 (3H, d, J=9 Hz), 3.1-3.4 (1H, m), 3.5-4.1 (11H, m), 4.3-4.5 (1H, m), 4.5-4.70H, m), 6.77 (1H, dd, J=2 Hz, J=9 Hz), 7.49 (1H, t, J=54 Hz), 7.62 (1H, d, J=9 Hz), 7.64 (1H, d, J=2 Hz).
MS m/z: 460 (M$^+$)

Production Example 9

2-(2-Difluoromethyl-6-ethoxybenzimidazol-1-yl)-4,6-dimorpholino-1,3,5-triazine (Compound 9)

Melting point: 222-224° C.
NMR (CDCl$_3$) δ: 1.46 (3H, t, J=7 Hz), 3.7-3.9 (16H, m), 4.08 (2H, q, J=7 Hz), 7.00 (1H, dd, J=9 Hz, 3 Hz), 7.52 (1H, t, J=54 Hz), 7.74 (1H, d, J=9 Hz), 7.89 (1H, d, J=3 Hz).
MS m/z: 461 (M$^+$)

Production Example 10

2-(2-Difluoromethyl-4-methylbenzimidazol-1-yl)-4,6-dimorpholino-1,3,5-triazine (Compound 10)

Melting point: 259-260° C.
NMR (CDCl$_3$) δ: 2.72 (3H, s), 3.7-3.9 (16H, m), 7.1-7.5 (2H, m), 7.56 (1H, t, J=54 Hz), 8.15 (1H, d, 8 Hz)
MS m/z: 431 (M$^+$)

Production Example 11

2-(2-Difluoromethyl-4-hydroxybenzimidazol-1-yl)-4-morpholino-6-(2,6-dimethylmorpholino)pyrimidine (Compound 11)

Melting point: 265-267° C.
$^1$H NMR (CDCl$_3$) δ: 3.7-3.9 (16 H, m), 3.86 (3 H, s), 7.02 (1 H, dd, J=3, 9 Hz), 7.52 (1H, t, J=53 Hz), 7.75 (1 H, d, J=9 Hz), 7.91 (1 H, d, J=3 Hz).
MS m/z 447 (M$^+$).

Production Example 12

2-(2-Difluoromethyl-5-hydroxybenzimidazol-1-yl)-4,6-dimorpholino-1,3,5-triazine (Compound 12)

Melting point: 272-274° C.
NMR (CDCl$_3$) δ: 3.7-3.9 (16H, m), 7.26-7.29 (2H, m), 7.54 (1H, t, J=54 Hz), 8.20 (1H, d, 8 Hz)
MS m/z: 433 (M$^+$)

Example 13

2-(6-Amino-2-difluoromethylbenzimidazol-1-yl)-4-(2,2-dimethylmorpholino)-6-morpholino-1,3,5-triazine (Compound 13)

Melting point: 226-227° C. (Decomposed)
NMR (CDCl$_3$) δ: 1.28 (6H, s), 3.6-3.8 (14H, m), 6.7-6.8 (1H, m), 7.2-7.7 (3H, m).
MS m/z: 460 (M$^+$)

Example 14

2-(4-Amino-2-difluoromethylbenzimidazol-1-yl)-4,6-dimorpholino-1,3,5-triazine (Compound 14)

Melting point: 214-216° C. (Decomposed)
NMR (CDCl$_3$) δ: 3.7-3.9 (16H, m), 4.48 (2H, brs), 6.63 (1H, d, J=8 Hz), 7.21 (1H, t, J=8 Hz), 7.55 (1H, t, J=54 Hz), 7.64 (1H, d, J=8 Hz).
MS m/z: 432 (M$^+$)

Production Example 15

2-(2-Difluoromethyl-4-hydroxybenzimidazol-1-yl)-4,6-dimorpholino-1,3,5-triazine (Compound 15)

Melting point: >250° C.
NMR (DMSO-d$_6$) δ: 3.70-3.90 (16H, m), 6.76 (1H, d, J=8 Hz), 7.73 (1H, t, J=8 Hz), 7.70 (1H, t, J=54 Hz), 7.74 (1H, d, J=8 Hz), 10.24 (1H, brs)
MS m/z: 433

Production Example 16

2-(2-Difluoromethyl-6-hydroxybenzimidazol-1-yl)-4,6-dimorpholino-1,3,5-triazine (Compound 16)

Melting point: >250° C.
NMR (DMSO-d$_6$) δ: 3.70-3.90 (16H, m), 6.86 (1H, d, J=8 Hz), 7.61 (1H, d, J=8 Hz), 7.70 (1H, t, J=54 Hz), 7.73 (1H, s), 9.81 (1H, brs)
MS m/z: 433

Production Example 17

2-(5-Amino-2-difluoromethylbenzimidazol-1-yl)-4,6-di(2,6-dimethylmorpholino)pyrimidine (Compound 17)

Melting point: 157-160° C.
NMR (CDCl$_3$) δ: 1.30 (6H, d, J=9 Hz), 2.6-2.8 (4H, m), 3.6-4.2 (8H, m), 5.45 (1H, s), 6.7-6.8 (1H, m), 7.5-7.7 (2H, m), 7.42 (1H, t, J=53 Hz)
MS m/z: 487 (M$^+$)

Production Example 18

2-(2-Difluoromethyl-4-hydroxybenzimidazol-1-yl)-4,6-dimorpholinopyrimidine (Compound 18)

Melting point: >250° C.
NMR (DMSO-d$_6$) δ: 3.60-3.80 (16H, m), 5.98 (1H, s), 6.72 (1H, d, J=8 Hz), 7.22 (1H, t, J=8 Hz), 7.62 (1H, d, J=8 Hz), 7.65 (1H, t, J=54 Hz), 10.17 (1H, brs)
MS m/z: 432

Production Example 19

2-(6-Amino-4-chloro-2-difluoromethylbenzimidazol-1-yl)-4-(2,2-dimethylmorpholino)-6-morpholino-1,3,5-triazine (Compound 19)

(1) 6-Amino-4-chloro-2-difluoromethylbenzimidazole (500 mg, 2.3 mmol) was dissolved in acetone (50 ml), 2,4-dichloro-6-morpholino-1,3,5-triazine (542 mg, 2.3 mmol) was added at −15° C., and potassium carbonate (500 mg) was further added. After having elevated the temperature gradually to room temperature, the mixture was stirred at room temperature for 5 hours. The solvent was evaporated under vacuum, and the residue was purified by silica gel column chromatography (n-hexane:ethyl acetate=1:4) to afford 2-(6-amino-4-chloro-2-difluoromethylbenzimidazol-1-yl)-4-chloro-6-morpholino-1,3,5-triazine (272 mg, yield 28%).

(2) 2-(6-Amino-4-chloro-2-difluoromethylbenzimidazol-1-yl)-4-chloro-6-morpholino-1,3,5-triazine (150 mg, 0.36 mmol) thus obtained was dissolved in DMF (6 ml), 2,2-dimethylmorpholine hydrochloride (150 mg, 10 mmol) was added thereto at −15° C., and potassium carbonate (500 mg) was further added. After stirring at room temperature overnight, water was added to the reaction mixture, which was extracted with ethyl acetate several times, washed with brine, and dried over anhydrous magnesium sulfate. After the solvent was evaporated under vacuum, the residue was purified by silica gel column chromatography (n-hexane:ethyl acetate=1:2) to give the title compound as colorless crystals (130 mg, yield 73%).

Melting point: 238° C. (Decomposed)
NMR (CDCl$_3$) δ: 1.27 (6H, s), 3.68 (2H, s), 3.7-3.9 (12H, m), 6.82 (1H, d, J=2.3 Hz), 7.42 (1H, dt, J=9.6 Hz, J=53 Hz), 7.50 (1H, d, J=2.3 Hz)
MS m/z: 494 (M$^+$)

Production Example 20

2-(2-Difluoromethyl-4-hydroxybenzimidazol-1-yl)-4-(2-hydroxymethylpyrrolidin-1-yl)-6-morpholino-1,3,5-triazine (Compound 20)

Melting point: 245° C. (Decomposed)
NMR (CDCl$_3$) δ: 1.9-2.1 (4H, m), 3.5-4.0 (12H, m), 4.7-4.8 (1H, m), 5.1-5.3 (1H, m), 6.89 (1H, d, J=9 Hz), 7.30 (1H, t, J=9 Hz), 7.50 (1H, brs), 7.55 (1H, t, J=54 Hz), 7.83 (1H, d, J=9 Hz).
MS m/z: 447 (M$^+$)

Production Example 21

2-(2-Difluoromethyl-4-hydroxybenzimidazol-1-yl)-4-(2,2-dimethylmorpholino)-6-morpholinopyrimidine (Compound 21)

Melting point: 185-187° C.
NMR (CDCl$_3$) δ: 1.29 (6H, s), 3.48 (2H, s), 3.59-3.64 (6H, m), 3.81-3.87 (6H, m), 5.47 (1H, s), 6.86 (1H, m), 7.26-7.32 (1H, m), 7.49 (1H, t, J=53 Hz), 7.72 (1H, d, 8 Hz)
MS m/z: 460 (M$^+$)

Production Example 22

2-(2-Difluoromethyl-4-hydroxybenzimidazol-1-yl)-4-(3,3-dimethylmorpholino)-6-morpholinopyrimidine (Compound 22)

Melting point: 204-206° C.

NMR (CDCl$_3$) δ: 1.48 (6H, s), 3.50 (2H, s), 3.6-3.8 (6H, m), 3.8-4.0 (6H, m), 5.76 (1H, s), 6.68 (1H, d, J=7 Hz), 7.29 (1H, d, J=7 Hz), 7.49 (1H, t, J=54 Hz), 7.66 (1H, d, 7 Hz)
MS m/z: 460 (M$^+$)

Production Example 23

2-(2-Difluoromethyl-5-methoxybenzimidazol-1-yl)-4,6-dimorpholino-1,3,5-triazine (Compound 23)

Melting points: 206-207° C.
NMR ((CD$_3$)$_2$CO) δ: 1.17 (6H, d, J=6 Hz), 2.5-2.8 (4H, m), 3.6-4.4 (10H, m), 5.95 (1H, s), 6.77 (1H, d, J=8 Hz), 7.23 (1H, t, J=8 Hz), 7.66 (1H, t, J=53 Hz), 7.75 (1H, d, J=8 Hz), 8.9 (1H, s)
MS m/z 447 (M$^+$)

Production Example 24

2-(2-Difluoromethyl-4-methoxybenzimidazol-1-yl)-4-(cis-2,6-dimethylmorpholino)-6-morpholinopyrimidine (Compound 24)

(1) 2-Difluoromethyl-4-methoxybenzimidazole (9.03 g, 45.6 mmol) was dissolved in DMF (100 ml), 60% NaH (1.82 g, 45.6 mmol) was added, and stirred for 30 minutes. The reaction mixture was added to a solution obtained by dissolving 2,4,6-trichloropyrimidine (15.7 g, 92.1 mmol) into DMF (100 ml) while cooling with ice, and stirred on an ice bath for 30 minutes and further at room temperature for 2 hours. Water was added to the reaction mixture, precipitated crystals were filtered, and washed well with hexane and ether, then air-dried to afford 2-(2-difluoromethyl-4-methoxybenzimidazol-1-yl)-4,6-dichloropyrimidine (12.3 g, yield 78%).
(2) 2-(2-Difluoromethyl-4-methoxybenzimidazol-1-yl)-4,6-dichloropyrimidine (12.3 g, 35.7 mmol) thus obtained was dissolved in DMF (150 ml), cis-2,6-dimethylmorpholine (6.63 ml, 53.7 mmol) was added at room temperature, and potassium carbonate (7.35 g) was further added. After stirring at room temperature for 30 minutes, water was added to the reaction mixture, extracted with ethyl acetate several times, washed with brine, and dried over anhydrous magnesium sulfate. After the solvent was evaporated under vacuum, the residue was washed sufficiently with hexane, and then successively with ether, and then air-dried to give 4-chloro-2-(2-difluoromethyl-4-methoxybenzimidazol-1-yl)-6-(cis-2,6-dimethyl-morpholino)pyrimidine (14.4 g, yield 95%).
(3) Morpholine (275 ml, 3.15 mol) was added to 4-chloro-2-(2-difluoromethyl-4-methoxybenzimidazol-1-yl)-6-(cis-2,6-dimethylmorpholino)pyrimidine (14.4 g, 34 mmol) thus obtained, and stirred at room temperature for 30 minutes and further at 80° C. for 30 minutes. Water was added to the reaction solution, and the precipitated crystals were filtered, and washed well successively with hexane, ether and ethyl acetate, then air-dried to afford 2-(2-difluoromethyl-4-methoxybenzimidazol-1-yl)-4-(cis-2,6-dimethylmorpholino)-6-morpholinopyrimidine (13.7 g, yield 86%).
Melting point: 180-181° C.
NMR (CDCl$_3$) δ: 1.28 (6H, d, J=6 Hz), 2.6-2.7 (2H, m), 3.6-3.7 (6H, m), 3.80-3.86 (4H, m), 4.04 (3H, s), 4.10-4.14 (2H, m), 5.49 (1H, s), 6.78 (1H, d, J=8 Hz), 7.32 (1H, d, J=8 Hz), 7.41 (1H, t, J=52 Hz), 7.77 (1H, d, J=8 Hz)
MS m/z: 474 (M$^+$)

Production Example 25

2-(2-Difluoromethylbenzimidazol-1-yl)-4-morpholino-6-(5-oxo-1,4-diazepan-1-yl)-1,3,5-triazine (Compound 25)

Melting point: 235-37° C.
$^1$H NMR (CDCl$_3$) δ: 2.7-2.8 (2H, m), 3.4-3.5 (2H, m), 3.8-4.2 (12H, m), 5.97 (1H, brs), 7.2-7.5 (2 H, m), 7.52 (1 H, t, J=54 Hz), 7.8-8.0 (1 H, m) 8.2-8.4 (1 H, m).
MS m/z 444 (M$^+$).

Production Example 26

2-(2-Difluoromethylbenzimidazol-1-yl)-4-(4-hydroxypiperizin-1-yl)-6-morpholino-1,3,5-triazine (Compound 26)

Melting point: 219-21° C.
$^1$H NMR (CDCl$_3$) δ: 3.4-3.5 (2H, m), 3.7-4.1 (16H, m), 7.3-7.5 (2 H, m), 7.59 (1 H, t, J=50 Hz), 7.8-8.0 (1 H, m) 8.3-8.4 (1 H, m).
MS m/z 431 (M$^+$).

Production Example 27

2-(2-Difluoromethylbenzimidazol-1-yl)-4-[4-(2-hydroxyethyl)piperazin-1-yl]-6-morpholino-1,3,5-triazine (Compound 27)

Melting point: 174-77° C.
$^1$H NMR (CDCl$_3$) δ: 2.6-2.7 (8H, m), 3.6-3.9 (12H, m), 3.91 (1H, br) 7.3-7.5 (2 H, m), 7.58 (1 H, t, J=54 Hz), 7.9-8.0 (1 H, m) 8.3-8.4 (1 H, m).
MS m/z 460 (M$^+$).
Refer to Patent Document 4.

Production Example 28

2-(2-Difluoromethyl-4-hydroxybenzimidazol-1-yl)-4-(2-hydroxymethylpyrrolidin-1-yl)-6-morpholinopyrimidine (1) 4-tert-Butyldimethylsilyloxy-2-difluoromethylbenzimidazole (1.49 g, 5.0 mmol) was dissolved in DMF (10 ml), 2,4,6-trichloropyrimidine (0.91 g, 5.0 mmol) was added at room temperature, potassium carbonate (0.55 g) was further added, and the mixture was stirred for 5 hours. Water was added to the reaction mixture, extracted with ethyl acetate several times, washed with brine, and then dried over anhydrous magnesium sulfate. After the solvent was evaporated under vacuum, the residue was purified by silica gel column chromatography (n-hexane:ethyl acetate=8:1) to give 2-(4-tert-buthyldimethylsilyloxy-2-difluoromethylbenzimidazol-1-yl)-4,6-dichloropyrimidine (1.12 g, yield 50%).
(2) 2-(4-tert-Buthyldimethylsilyloxy-2-difluoromethylbenzimidazol-1-yl)-4,6-dichloropyrimidine (386 mg, 0.87 mmol) thus obtained was dissolved in DMF (6 ml), 2-pyrrolidine methanol (0.13 ml, 1.3 mmol) was added at room temperature, and potassium carbonate (179 mg) was further added. After the mixture was stirred at room temperature for 30 minutes, water was added to the reaction mixture, extracted with ethyl acetate several times, washed with brine, and dried over anhydrous magnesium sulfate. After the solvent was evaporated under vacuum, the residue was purified by silica gel column chromatography (n-hexane:ethyl acetate=1:1) to give 2-(4-tert-buthyldimethylsilyloxy-2-difluoromethylbenzimidazol-1-yl)-4-(2-hydroxy-methylpyrrolidin-1-yl)-6-chloropyrimidine (291 mg, yield 64%).

(3) Morpholine (4.4 g, 50 mmol) was added to 2-(4-tert-buthyldimethylsilyloxy-2-difluoromethylbenzimidazol-1-yl)-4-(2-hydroxymethyl-pyrrolidin-1-yl)-6-chloropyrimidine (281 mg, 0.54 mmol) thus obtained, and the mixture was stirred at room temperature for 9 hours. Water was added to the reaction mixture, extracted with ethyl acetate several times, washed with brine, and then dried over anhydrous magnesium sulfate. After the solvent was evaporated under vacuum, the residue was purified by silica gel column chromatography (n-hexane:ethyl acetate=2:3) to obtain 2-(4-tert-buthyldimethylsilyloxy-2-difluoromethylbenzimidazol-1-yl)-4-(2-hydroxymethylpyrrolidin-1-yl)-6-morpholinopyrimidine (216 mg, yield 72%).

2-(4-tert-Buthyldimethylsilyloxy-2-difluoromethyl-benzimidazol-1-yl)-4-(2-hydroxymethylpyrrolidin-1-yl)-6-morpholinopyrimidine (213 mg, 0.38 mmol) was dissolved in anhydrous THF (7 ml), tetra-n-butylammonium fluoride (0.4 ml) (1M THF solution) was added at room temperature, and the mixture was stirred for 30 minutes. Water was added to the reaction mixture, extracted with ethyl acetate several times, washed with brine, and dried over anhydrous magnesium sulfate. After the solvent was evaporated under vacuum, the residue was purified by silica gel column chromatography (n-hexane:ethyl acetate=1:4) to obtain the title compound as colorless crystals (101 mg, yield 60%).

Melting point: 195-198° C.
NMR (CDCl$_3$) δ: 2.0-2.1 (4H, m), 3.4-4.0 (12H, m), 4.0-4.1 (1H, m), 4.3-4.4 (1H, m), 5.36 (1H, s), 6.85 (1H, d, J=8 Hz), 7.28 (1H, t, J=8 Hz), 7.58 (1H, brs), 7.58 (1H, t, J=54 Hz), 7.73 (1H, d, J=8 Hz).
MS m/z: 446 (M$^+$)

The production was effected with reference to Patent Document 4.

Production Example 29

2-(5,6-Dimethyl-2-difluoromethylbenzimidazol-1-yl)-4,6-dimorpholino-1,3,5-triazine Melting point: 217-220° C.
$^1$H NMR (CDCl$_3$) δ: 2.39 (3H, s), 2.40 (3H, s), 3.7-3.9 (16H, m), 7.53 (1H, t, J=54 Hz), 7.62 (1H, s) 8.12 (1H, s).
MS m/z 445 (M$^+$).

Production Example 30

2-(6-Amino-4-chloro-2-difluoromethylbenzimidazol-1-yl)-4-(2-hydroxymethylpyrrolidin-1-yl)-6-morpholino-1,3,5-triazine Melting point: 256° C. (Decomposed)
NMR (CD$_3$OD-CDCl$_3$ (1:1)) δ: 1.9-2.2 (4H, m), 3.68 (2H, s), 3.5-4.0 (11H, m), 4.39 (1H, brs), 6.84 (1H, d, J=2.1 Hz), 7.58 (1H, t, J=53 Hz), 7.64 (1H, d, J=2.1 Hz).
MS m/z: 480 (M$^+$)

Production Example 31

2-(4-Chloro-2-difluoromethyl-5-hydroxybenzimidazol-1-yl)-4,6-dimorpholino-1,3,5-triazine Melting point: >250° C.

NMR (CDCl$_3$) δ: 3.7-3.9 (16H, m), 5.63 (1H, s), 7.15 (1H, d, J=9 Hz), 7.51 (1H, t, J=53 Hz), 8.14 (1H, d, J=9 Hz).
MS m/z: 467 (M$^+$)

Production Example 32

Synthesis of 4-(4-acetylpiperazin-1-yl)-2-(2-difluoromethylbenzimidazol-1-yl)-6-morpholino-1,3,5-triazine (Compound 28)

A mixture of 6-chloro-2-(2-difluoromethylbenzimidazol-1-yl)-4-morpholino-1,3,5-triazine (3.66 g, 10 mmol), 1-acetylpiperazine (1.40 g, 11 mmol), potassium carbonate (1.38 g, 10 mmol) and DMF (30 ml) was stirred at room temperature for 16 hours. The reaction mixture was poured into water, and extracted with dichloromethane. The extract was dried over anhydrous sodium sulfate, concentrated under vacuum, and the residue was purified by silica gel column to obtain 4-(4-acetylpiperazin-1-yl)-2-(2-difluoromethylbenzimidazol-1-yl)-6-morpholino-1,3,5-triazine (4.08 g, 9.0 mmol) in a yield of 90% as colorless crystals.

Naturally, triazine or pyrimidine derivatives bearing such piperazine groups may also be synthesized according to the following schemes.

For example, a mixture of 6-chloro-2-(2-difluoromethylbenzimidazol-1-yl)-4-morpholino-1,3,5-triazine (3.66 g, 10 mmol), piperazine (3.45 g, 40 mmol), and acetone (50 ml) was stirred at room temperature for 16 hours. The reaction mixture was poured into water, and precipitated crystals were filtered, and washed with methanol to afford 2-(2-difluoromethylbenzimidazol-1-yl)-4-morpholino-6-(piperazin-1-yl)-1,3,5-triazine (3.87 g, 9.3 mmol) in a yield of 93% as colorless crystals.

$^1$H NMR (CDCl$_3$) δ: 3.8-4.1 (16H, m), 7.3-7.5 (2 H, m), 7.59 (1 H, t, J=54 Hz), 7.9-8.0 (1 H, m) 8.3-8.4 (1 H, m).
MS m/z 416 (M$^+$).

Acetyl chloride (0.14 ml, 2.0 mmol) was added dropwise to a mixture of 2-(2-difluoromethylbenzimidazol-1-yl)-4-morpholino-6-(piperazin-1-yl)-1,3,5-triazine (417 mg, 1.0 mmol) and THF (10 ml). The reaction mixture was stirred at room temperature for 22 hours. The reaction mixture was poured into water, and extracted with dichloromethane. The extract was dried over anhydrous sodium sulfate, concentrated under vacuum, and the residue was purified by silica gel column to give the target compound 4-(4-acetylpiperazin-1-yl)-2-(2-difluoromethylbenzimidazol-1-yl)-6-morpholino-1,3,5-triazine (354 mg, 7.7 mmol) in a yield of 77% as colorless crystals.

Melting point: 223° C.
$^1$H NMR (CDCl$_3$) δ: 2.18 (3 H, s), 3.6-4.0 (16H, m), 7.3-7.5 (2 H, m), 7.55 (1 H, t, J=53.5 Hz), 7.9-8.0 (1 H, m) 8.3-8.4 (1 H, m).
MS m/z 458 (M$^+$).

The following compounds were manufactured in a manner similar to Production Example 34.

Production Example 33

2-(2-Difluoromethylbenzimidazol-1-yl)-6-(4-formylpiperazin-1-yl)-4-morpholino-1,3,5-triazine Melting point: 228-30° C.
$^1$H NMR (CDCl$_3$) δ: 3.8-4.1 (16H, m), 7.2-7.5 (2 H, m), 7.54 (1 H, t, J=54 Hz), 7.8-8.0 (1H, m), 8.17 (1H, s), 8.3-8.4 (1 H, m).
MS m/z 444 (M$^+$).

Production Example 34

2-(2-Difluoromethylbenzimidazol-1-yl)-4-morpholino-6-(3-oxopiperazin-1-yl)-1,3,5-triazine Melting point: 255-57° C.
$^1$H NMR (CDCl$_3$) δ: 3.5-3.9 (14H, m), 6.48 (1H, brs), 7.2-7.5 (2 H, m), 7.59 (1 H, t, J=54 Hz), 7.8-7.9 (1 H, m) 8.2-8.4 (1 H, m).
MS m/z 430 (M$^+$).

Production Example 35

2-(2-Difluoromethylbenzimidazol-1-yl)-6-(3,5-dioxopiperazin-1-yl)-4-morpholino-1,3,5-triazine Melting point: 230-32° C.
$^1$H NMR (CDCl$_3$) δ: 3.5-3.9 (12H, m), 7.2-7.5 (2 H, m), 7.59 (1 H, t, J=55 Hz), 7.9-8.0 (1H, m) 8.3-8.4 (1 H, m).
MS m/z 444 (M$^+$).

Production Example 36

2-(2-Difluoromethylbenzimidazol-1-yl)-4-(4-benzylcarbonylpiperazin-1-yl)-6-morpholino-1,3,5-triazine (Compound 29)

Melting point: 178-181° C.
$^1$H NMR (CDCl$_3$) δ: 3.81 (2 H, s), 3.5-3.9 (16 H, m), 7.2-7.5 (7 H, m), 7.52 (1 H, t, J=54 Hz), 7.89 (1 H, d, J=8 Hz), 8.30 (1 H, d, J=8 Hz).
MS m/z 534 (M$^+$).

Production Example 37

4-(4-Acetonylpiperazin-1-yl)-2-(2-difluoromethylbenzimidazol-1-yl)-6-morpholino-1,3,5-triazine (Compound 30)

Melting point: 79-81° C.
NMR (CDCl$_3$) δ: 2.19 (3H, s), 2.60 (2H, s), 3.70-4.00 (16H, m), 7.30-7.50 (2H, m), 7.57 (1H, t, J=54 Hz), 7.90 (1H, d, J=8 Hz), 8.33 (1H, d, J=8 Hz)
MS m/z: 472

Production Example 38

2-(2-Difluoromethylbenzimidazol-1-yl)-4-[4-(2-furoyl)piperazin-1-yl]-6-morpholino-1,3,5-triazine (Compound 31)

Melting point: 220-222° C.
NMR (CDCl$_3$) δ: 3.80-4.00 (16H, m), 6.53 (1H, d, J=2 Hz), 7.01 (1H, d, J=2 Hz), 7.30-7.60 (4H, m), 7.80 (1H, d, J=8 Hz), 8.34 (1H, d, J=8 Hz)
MS m/z: 510

Production Example 39

2-(2-Difluoromethylbenzimidazol-1-yl)-4-[4-(N,N-dimethylcarbamoyl)piperazin-1-yl]-6-morpholino-1,3,5-triazine (Compound 32)

Melting point: 203-205° C.
NMR (CDCl$_3$) δ: 2.90 (6H, s), 3.30-3.40 (4H, m), 3.80-4.00 (12H, m), 7.30-7.40 (2H, m), 7.56 (1H, t, J=54 Hz), 7.89 (1H, d, 8 Hz), 8.34 (1H, d, 8 Hz)
MS m/z: 487

Production Example 40

2-(2-Difluoromethylbenzimidazol-1-yl)-4-(4-methoxylacetylpiperazin-1-yl)-6-morpholino-1,3,5-triazine (Compound 33)

Melting point: 72-75° C.
NMR (CDCl$_3$) δ: 3.46 (3H, s), 3.60-4.00 (16H, s), 4.17 (2H, s) 7.30-7.50 (2H, m), 7.55 (1H, t, J=54 Hz), 7.90 (1H, d, J=8 Hz), 8.34 (1H, d, J=8 Hz)
MS m/z: 488

Production Example 41

2-(2-Difluoromethylbenzimidazol-1-yl)-4-[4-(3-hydroxypropyl)piperazin-1-yl]-6-morpholino-1,3,5-triazine (Compound 34)

NMR (CDCl$_3$) δ: 1.17 (2H, m), 2.60-2.70 (4H, m), 4.70 (1H, brs) 3.50-4.00 (16H, m), 7.30-7.50 (2H, m), 7.56 (1H, t, J=54 Hz), 7.90 (1H, d, J=8 Hz), 8.33 (1H, d, J=8 Hz)
MS m/z: 474

Production Example 42

2-(2-Difluoromethylbenzimidazol-1-yl)-4-morpholino-6-(4-propionylpiperazin-1-yl)-1,3,5-triazine (Compound 35)

Melting point: 198-202° C.
NMR (CDCl$_3$) δ: 1.20 (3H, t, J=7 Hz), 2.42 (2H, q, J=7 Hz), 3.50-4.00 (16H, m), 7.30-7.50 (2H, m), 7.56 (1H, t, J=54 Hz), 7.90 (1H, d, J=8 Hz), 8.33 (1H, d, J=8 Hz)
MS m/z: 472

Production Example 43

2-(2-Difluoromethylbenzimidazol-1-yl)-4-(4-methoxycarbonylpiperazin-1-yl)-6-morpholino-1,3,5-triazine Melting point: 255-260° C.
NMR (CDCl$_3$) δ: 3.59 (4H, brs), 3.76 (3H, s), 3.70-3.95 (12H, s), 7.30-7.50 (2H, m), 7.55 (1H, t, J=54 Hz), 7.90 (1H, d, J=8 Hz), 8.34 (1H, d, J=8 Hz)
MS m/z: 474

The following were produced in the same manner as in Production Example 24.

Production Example 44

2-(2-Difluoromethyl-4-methoxybenzimidazol-1-yl)-4-(2,2-dimethylmorpholino)-6-morpholinopyrimidine (Compound 36)

Melting point: 166-168° C.
NMR (CDCl$_3$) δ: 1.30 (6H, s), 3.49 (2H, s), 3.4-3.9 (12H, m), 4.05 (3H, s), 5.47 (1H, s), 6.79 (1H, d, J=8 Hz), 7.32 (1H, t, J=8 Hz), 7.41 (1H, t, J=54 Hz), 7.78 (1H, d, J=8 Hz).
MS m/z: 474 (M$^+$)

Production Example 45

2-(2-Difluoromethyl-4-methoxybenzimidazol-1-yl)-4-(cis-2,3-dimethylmorpholino)-6-morpholinopyrimidine (Compound 37)

Melting point: 176-178° C.

NMR (CDCl$_3$) δ: 1.20 (3H, d, J=5 Hz), 1.22 (3H, d, J=5 Hz), 3.6-3.7 (1H, m), 3.6-4.1 (13H, m), 4.05 (3H, s), 5.47 (1H, s), 6.79 (1H, d, J=8 Hz), 7.32 (1H, t, J=8 Hz), 7.42 (1H, t, J=53 Hz), 7.78 (1H, d, J=8 Hz).

MS m/z: 474 (M$^+$)

Production Example 46

2-(2-Difluoromethyl-4-ethoxybenzimidazol-1-yl)-4-(2,2-dimethylmorpholino)-6-morpholinopyrimidine (Compound 38)

Melting point: 114-116° C.

NMR (CDCl$_3$) δ: 1.31 (6H, s), 1.56 (3H, t, J=7 Hz), 3.49 (2H, s), 3.5-3.9 (12H, m), 4.32 (2H, q, J=7 Hz), 5.47 (1H, s), 6.78 (1H, d, J=8 Hz), 7.30 (1H, t, J=8 Hz), 7.41 (1H, t, J=53 Hz), 7.76 (1H, d, J=8 Hz).

MS m/z: 488 (M$^+$)

Drug Efficacy Assays

Next, the assay protocols for pharmacological effects and toxicity of the heterocyclic compounds represented by the general Formula (I) and their results will be hereinafter described. Here, the compound number for each test substances corresponds to the compound number assigned to each of the above heterocyclic compounds.

Assay Example 1

Proliferation Inhibition. Assay for Mouse Spleen Cells

Spleen cells (2×10$^6$ cells/mL) prepared from C57BL/6N female mice (8 weeks old, purchased from Charles River Laboratories Japan Inc.) were suspended in RPMI 1640 medium (containing 10% fetal bovine serum, 10 mM HEPES, 1 mM pyruvic acid, 4.5 g/L glucose, 100 units/mL penicillin, and 0.1 mg/mL streptomycin), and seeded in wells of a 96 well plate at 0.225 mL per well. Serial dilutions of test substances were added to respective wells, and then concanavalin A (Con A, 3 μg/mL), lipopolysaccharide (LPS, 100 μg/mL), or an anti-mouse IgM antibody (100 μg/mL) were added. Thereafter, they were incubated under conditions of carbon dioxide 5% at a temperature 37° C. for 3 days. Next, Alamar Blue solution was added at 50 μL per 150 μL, and after having cultured for one day, the fluorescence intensity at 590 nm using an excitation wavelength of 530 nm was determined by Cytoflour 4000 (Applied Biosystems). As a result, as shown in Table 1, it was revealed that s-triazine analogs inhibit proliferation of mouse spleen cells induced by Con A, LPS, or an anti-IgM antibody.

TABLE 1

| Test Compounds | Inhibition of Con A response | Inhibition of LPS response | Inhibition of Anti-IgM antibody response |
|---|---|---|---|
| Compound 1 | + | + | nd |
| Compound 2 | + | + | + |
| Compound 3 | + | + | nd |
| Compound 4 | ++ | ++ | ++ |
| Compound 5 | + | + | + |
| Compound 6 | + | + | + |
| Compound 7 | + | + | + |
| Compound 8 | ++ | + | ++ |
| Compound 9 | ++ | ++ | ++ |
| Compound 10 | + | ± | + |
| Compound 12 | ++ | ++ | ++ |
| Compound 13 | ++ | ++ | ++ |
| Compound 17 | + | ± | + |
| Compound 19 | ++ | ++ | nd |
| Compound 20 | +++ | +++ | +++ |
| Compound 21 | +++ | +++ | +++ |

TABLE 1-continued

| Test Compounds | Inhibition of Con A response | Inhibition of LPS response | Inhibition of Anti-IgM antibody response |
|---|---|---|---|
| Compound 22 | +++ | +++ | +++ |
| Compound 24 | + | + | + |
| Compound 25 | ++ | + | nd |
| Compound 26 | +++ | ++ | nd |
| Compound 27 | +++ | + | nd |
| Compound 28 | +++ | ++ | nd |

Evaluation Criteria:
±: 10 μM < IC50 ≦ 100 μM
+: 0.1 μM < I C50 ≦ 10 μM
++: 0.001 μM < IC50 ≦ 0.1 μM
+++: IC50 ≦ 0.001 μM
nd: not tested Assay Example 2

Proliferation Inhibition Assay for Human Peripheral Blood Mononuclear Cells 4 mL of blood collected from healthy subjects was placed on 3 mL of MonoPoly Resolving Medium, and after centrifugation, the mononuclear cell (PBMC) fraction was collected. After washing with saline, PBMC (1×10$^5$ cells/mL) was suspended in RPMI 1640 medium (containing 10% fetal bovine serum, 10 mM HEPES, 1 mM pyruvic acid, and 4.5 g/L glucose). Next, after having added an anti-CD28 antibody (1 μg/mL) to the suspension, they were seeded on an anti-human CD3 T cell activation plate (BD Bioscience) at a capacity of 0.135 mL per well. Then, serial dilutions of test substances were added to respective wells, and incubated under conditions of carbon dioxide 5% at a temperature 37° C. After 3 days, Alamar Blue solution was added at 50 μL per well, and after incubation for one day, a fluorescence intensity at 590 nm using an excitation wavelength of 530 nm was determined by Cytoflour 4000 (Applied Biosystems). As a result, as shown in Table 2, it was revealed that s-triazine analogs inhibit the growth of human T cells induced by an anti-CD3 antibody and an anti-CD28 antibody.

TABLE 2

| Test Compounds | IC50 (μM) |
|---|---|
| Compound 1 | 1.780 |
| Compound 3 | 1.130 |
| Compound 4 | 0.312 |
| Compound 6 | 2.08 |
| Compound 10 | 0.825 |
| Compound 11 | >10 |
| Compound 14 | 0.0923 |
| Compound 15 | 0.00291 |
| Compound 16 | 0.0123 |
| Compound 20 | 0.00815 |
| Compound 23 | 0.0192 |
| Compound 24 | 0.471 |

Assay Example 3

Activation Inhibition Assay for Human Peripheral Blood Mononuclear Cells

In accordance with the method of Assay Example 2, PBMC (2×10$^6$ cells/mL) was isolated from human peripheral blood, suspended in RPMI 1640 medium (containing 10% fetal bovine serum, 10 mM HEPES, 1 mM pyruvic acid, and 4.5 g/L glucose), and seeded in wells of a 96 well plate at 0.225 mL per well. The test substances were added to respective wells, and then an anti-CD3 antibody (2 μg/mL) and an anti-CD28 antibody (1 μg/mL) were added. Then, after incubation under conditions of carbon dioxide 5% at a temperature 37° C. for 6 hours, the expressions of CD40L and CD69, activation markers, were analysed by flow cytometry. As a result, when the cells were stimulated by both an anti-CD3 antibody and an anti-CD28 antibody, CD40L was expressed on 14.4% of PBMC, which was also CD4 positive. However, the proportion of the cells which expressed CD40L decreased when the cells had been treated with test substances (Compound 4: 4.9%; Compound 20: 3.7%, Compound 24: 3.6%). Although CD69 was expressed on 28.8% (CD4-positive) and 50.9% (CD4-negative) of PBMC, the proportions of CD4-positive cells (Compound 4: 18.8%, Compound 20: 10.1%, Compound 24: 17.7%) and CD4-negative cells (Compound 4: 17.7%, Compound 20: 10.5%, Compound 24: 22.4%) which expressed CD69 decreased when the cells had been treated with test substances. Thus, the s-triazine analogs were shown to inhibit the activation of lymphocytes (FIGS. 1A, 1B, 1C and 1D).

Assay Example 4

Adjuvant-Induced Arthritis Inhibitory Action

Figure 2:
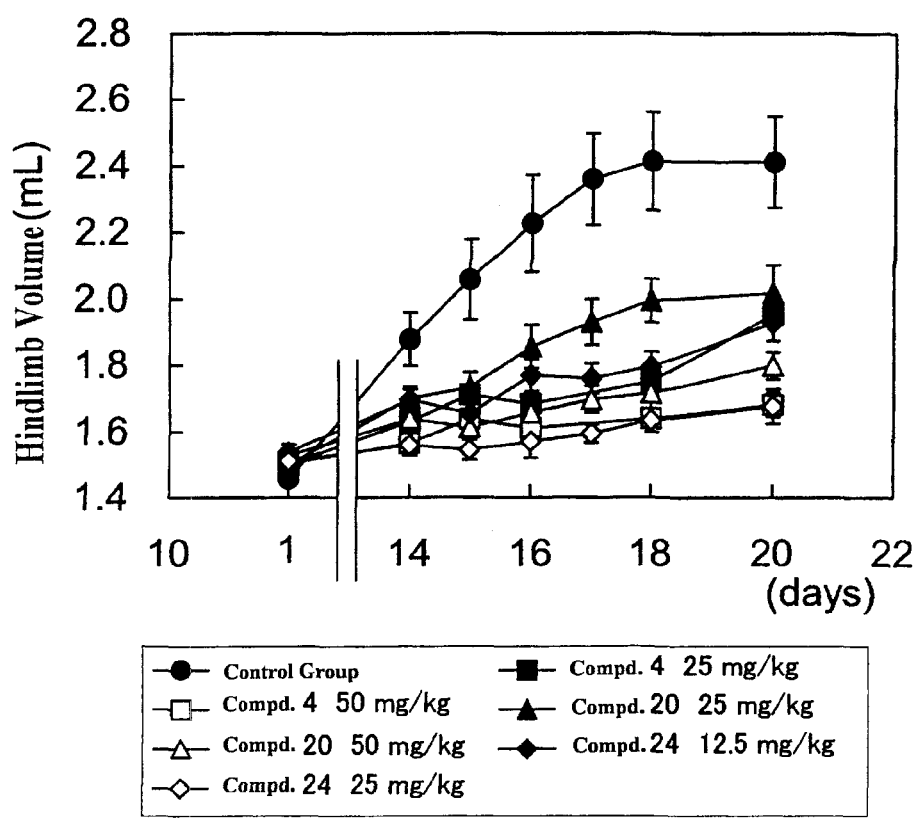
[FIG. 2] Graph depicting a comparison between test substance-treated group and control group on the volume change in hind paw of rats after the onset of adjuvant-induced arthritis.

Lyophilized *Mycobacterium butyricum* suspended in Freund's incomplete adjuvant was intradermally administered to the base of the tail of Lewis male rats (7 weeks old, purchased from Charles River Laboratories Japan Inc.) to induce adjuvant-induced arthritis. Then, 10 days after the induction of the adjuvant-induced arthritis, the test substances suspended in 0.5% hydroxypropylcellulose (HPC) were orally administered on consecutive days. Furthermore, after the onset of the arthritis, the volume of the hind paw was measured using a hindpaw edema volume measuring apparatus (TK105, Physio-Tech). As a result, for the test substances, as shown in FIG. 2, a statistically significant (analysis of variance, Dunnett's test P<0.05) effect in comparison with the control group after day 14 was confirmed for the present model study.

Assay Example 5

Collagen-Induced Arthritis Inhibitory Action

Figure 3:
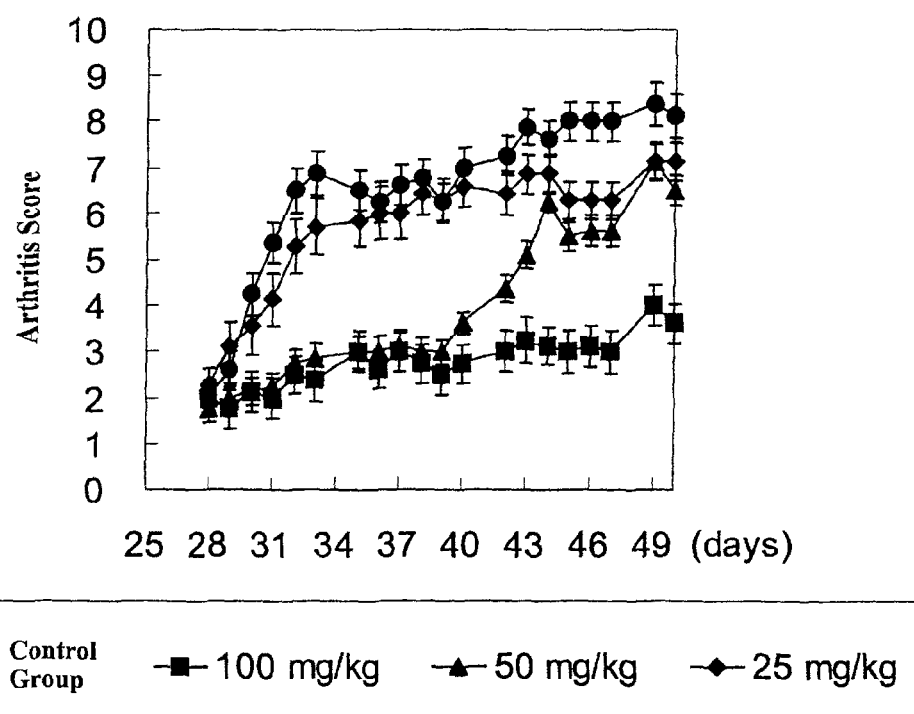
[FIG. 3] Graph depicting a comparison between test substance-treated group and control group on the change in arthritis score after the onset of collagen-induced arthritis.

Bovine type II collagen suspended in Freund's complete adjuvant was intradermally administered to the base of tail of DBA1 male mice (7 weeks old, purchased from Charles River Laboratories Japan Inc.) on day 1 and day 21. Then, from day 28 when 50% of the mice developed arthritis, the test substances suspended in 0.5% hydroxypropylcellulose (HPC) were orally administered on consecutive days. Here, the efficacy was evaluated by scoring the arthritis. Specifically, for each paw, the degree of arthritis was evaluated according to: no symptoms: 0; redness or swelling of one joint: 1; redness or swelling for two or more joints: 2; redness or swelling over the entire paw: 3; and maximum redness or swelling over the entire paw: 4. As a result, it was revealed that Compound 4 inhibited the progression of the collagen-induced arthritis in a dose-dependent manner. For the group administered 50 or 100 mg/kg of the above compound, after day 30, a statistically significant efficacy was recognized (Dunnett's test P<0.05). However, for the group administered 50 mg/kg of the above compound, the conditions were exacerbated after day 40, and no significant difference was recognized in comparison with the control group after day 44 (FIG. 3).

Assay Example 6

Inhibition Assay for Proliferation of Rabbit Synoviocyte

Rabbit synoviocytes HIG-82 suspended in HAM medium (containing 10% fetal bovine serum, 25 mM HEPES, and 0.1 mg/mL kanamycin) (with $4 \times 10^4$ cells/mL) were seeded in wells of a 96 well plate at 0.135 mL per well. Then, 15 µL of each of serial dilutions of test substances was added to a respective well, and incubated under conditions of carbon dioxide 5% at a temperature 37° C. Alamar Blue solution was added at 50 µL per well on day 0 and day 3, and incubated for one day, and thereafter fluorescence intensity at 590 nm using an excitation wavelength of 530 nm was determined by Cytoflour 4000 (Applied Biosystems). As shown in Table 3, it was demonstrated that s-triazine analogs inhibited cell division of rabbit synoviocytes.

TABLE 3

| Test Compounds | IC50 (µM) |
|---|---|
| Compound 1 | 4.85 |
| Compound 3 | 1.78 |
| Compound 4 | 0.953 |
| Compound 6 | 6.35 |
| Compound 10 | 6.51 |
| Compound 11 | >10 |
| Compound 14 | 0.484 |
| Compound 15 | 0.0856 |
| Compound 16 | 0.163 |
| Compound 20 | 0.122 |
| Compound 23 | 0.121 |
| Compound 24 | 0.441 |
| Compound 25 | 0.990 |
| Compound 26 | 2.38 |
| Compound 27 | 1.56 |
| Compound 28 | 1.11 |

Assay Example 7

Allogeneic Mixed Lymphocyte Reaction

Spleen cells prepared from C57BL/6N female mice (8-10 weeks old, purchased from Charles River Laboratories Japan Inc.) and peripheral lymph node mononuclear cells prepared from BALB/c female mice (8-10 weeks old, purchased from Charles River Laboratories Japan Inc.) were used as stimulator cells and responder cells, respectively. The respective cells were suspended in RPMI 1640 medium (containing 10% fetal bovine serum, 100 units/mL penicillin, and 0.1 mg/mL streptomycin) (with $2 \times 10^6$ cells/mL). Then, the stimulator cells (50 µL) treated with mitomycin C (50 µg/mL, 30 minutes) were added to the responder cells (100 pp. Thereafter, serial dilutions of test substances were added to respective wells, and incubated under conditions of carbon dioxide 5% at 37° C. for 86 hours. Finally, the cell proliferation was examined using a BrdU cell proliferation kit (Calbiochem). As a result, as shown in Table 4, it was found that the s-triazine analogs inhibited the allogeneic mixed lymphocyte reaction.

TABLE 4

| Test Compounds | IC50 (µM) |
|---|---|
| Compound 1 | 0.670 |
| Compound 3 | 0.600 |
| Compound 4 | 0.218 |
| Compound 6 | 3.63 |
| Compound 10 | 0.344 |
| Compound 11 | 1.43 |
| Compound 14 | 0.227 |
| Compound 15 | 0.0421 |
| Compound 16 | 0.46 |
| Compound 20 | 0.136 |
| Compound 23 | 0.258 |
| Compound 24 | 0.286 |

Assay Example 8

Proliferation Inhibitory Activity on Hematologic Neoplasm Cells

Daudi cells ($5 \times 10^5$ cells/mL), Jurkat cells ($5 \times 10^5$ cells/mL), THP-1 cells ($5 \times 10^5$ cells/mL), U 937 cells ($5 \times 10^5$ cells/mL), and HL 60 cells ($5 \times 10^5$ cells/mL) suspended in RPMI 1640 medium (containing 10% fetal bovine serum, 10 mM HEPES, 1 mM pyruvic acid, 4.5 g/L glucose, 100 units/mL penicillin, and 0.1 mg/mL streptomycin) were seeded in 96 well plates at a capacity of 0.135 mL per well. Serial dilutions of test substances were added to respective wells at 15 µL/well, and incubated under conditions of carbon dioxide 5% at 37° C. for 3 days. Thereafter, Alamar Blue solution was added at 50 µL, and after incubation for one day, the fluorescence intensity at 590 nm using an excitation wavelength of 530 nm was determined by Cytoflour 4000 (Applied Biosystems). As a result, as shown in Table 5, it was revealed that s-triazine analogs inhibited the proliferation of hematologic neoplasm cells.

TABLE 5

| Test Compounds | Daudi | Jurkat | HL60 | THP-1 | IC$_{50}$(µM) U937 |
|---|---|---|---|---|---|
| Compound 1 | 0.827 | 5.02 | >10 | 0.535 | >10 |
| Compound 3 | 0.379 | 3.27 | 3.16 | 0.135 | 4.14 |
| Compound 4 | 0.105 | 1.95 | 1.12 | 0.511 | 3.24 |
| Compound 6 | 0.803 | 6.62 | >10 | 5.54 | >10 |
| Compound 10 | 0.16 | >10 | 1.79 | 0.794 | >10 |
| Compound 11 | 2.75 | >10 | >10 | >10 | >10 |
| Compound 14 | 0.0655 | 1.34 | 0.396 | 0.286 | 1.11 |
| Compound 15 | 0.00492 | 0.116 | 0.0358 | 0.0454 | 0.217 |
| Compound 16 | 0.0103 | 0.357 | 0.0672 | 0.112 | 0.604 |
| Compound 19 | 0.0212 | 1.6 | Nd | 0.12 | Nd |
| Compound 20 | 0.00823 | 0.196 | 0.0745 | 0.044 | 0.252 |
| Compound 23 | 0.0132 | 0.229 | 0.139 | 0.0686 | 0.3454 |
| Compound 24 | 0.397 | 1.45 | 0.823 | 0.859 | 2.79 |
| Compound 25 | 0.19 | 1.59 | Nd | 0.379 | Nd |
| Compound 26 | 0.426 | 3.12 | Nd | 0.865 | Nd |
| Compound 27 | 0.324 | 3.60 | Nd | 0.73 | Nd |
| Compound 28 | 0.235 | 1.80 | Nd | 0.496 | Nd |

Nd: not tested.

Assay Example 9

Therapeutic Action on Human B Lymphoma Xenografted Model

Figure 4:
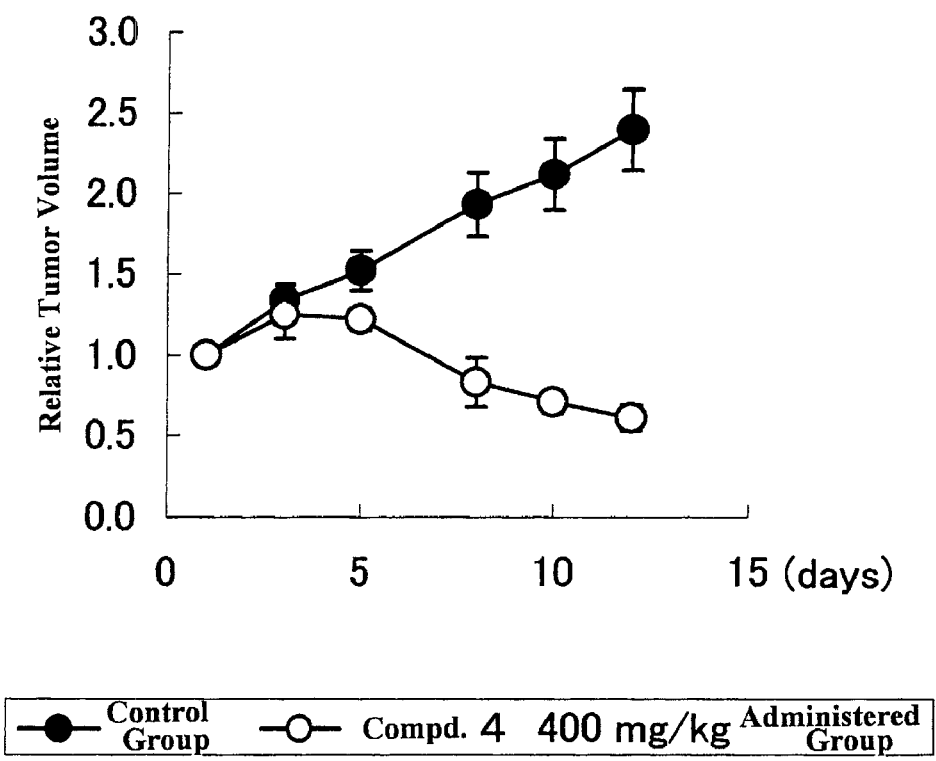
[FIG. 4] Graph depicting a comparison between test substance-treated group and control group in a human B lymphoma xenografted model.

Daudi cells ($1 \times 10^7$ cells/mL) cultured in RPMI 1640 medium (containing 10% fetal bovine serum, 10 mM HEPES, 1 mM pyruvic acid, 4.5 g/L glucose, 100 units/mL penicillin, and 0.1 mg/mL streptomycin) were implanted subcutaneously in the chests of 8 week-old NOD/SCID mice. After day 20 when the tumor had grown to the volume of about 800 mm$^3$, Compound 4 (400 mg/kg) was administered orally. As a result, as shown in FIG. 4, the increase in tumor volume in the present model was inhibited.

Assay Example 10

Fulminant Hepatitis Model

BALB/c male mice (7 weeks old, purchased from Charles River Laboratories Japan Inc.) were used in the experiment. After having orally administered the test substances suspended in 5% HPC, galactosamine (800 mg/kg) and LPS (110 µg/kg) were intraperitoneally administered. Then, survival rates at 72 hours after administration were obtained. As a result, as shown in Table 6, the test substances improved the survival rate due to galactosamine and LPS.

TABLE 6

| | Survival Rate after 72 Hours | |
|---|---|---|
| Test Compounds | 50 mg/kg | 100 mg/kg |
| Compound 4 | 60% | 83% |
| Compound 6 | — | 40% |
| Compound 15 | 17% | 0% |
| Compound 18 | 50% | 80% |
| Compound 20 | 17% | 72% |
| Compound 24 | 33% | 67% |

Assay Example 11

Toxicologic Test for Single Oral Administration

A single oral dose toxicity of typical heterocyclic compounds was examined using SD male rats (6 weeks old, weight 162-188 g), and as a result, for Compound 4, no examples of death were recognized even with 1200 mg/kg, and for Compound 24, LD$_{50}$ was 600-900 mg/kg.

Assay Example 12

Ames Test

Using 5 strains of *Salmonella typhimurium* TA98, TA100, TA1535, TA1537 and *Escherichia coli* WP2uvrA, the test substances (Compound 4, Compound 19, Compound 22 and Compound 24) were tested for their mutagenesis according to a preincubation method. As a result, with or without metabolic activation due to S-9, even in 5000 µg/flat plate (maxium dose), no increase was observed in the colony number of reverse mutation in any tested strains, so mutagenesis was negative. Accordingly, in addition to in vivo tests such as rat adjuvant induced arthritis assay, mouse collagen induced arthritis assay, human B-lymphoma xenografted model, fulminant hepatitis inhibition assay and toxicologic test for single oral administration, s-triazine analogs were found to be safer compounds.

The agents of the present invention inhibit the response to T cells and B cells induced by ConA, LPS, anti-IgM antibody, anti-CD3 antibody+anti-CD28 antibody, thereby exhibiting PI3K inhibitory action on immune cells. Specifically, the drugs of the present invention can be used in the treatment and prevention of disorders of immune system attributable to the hyperfunctioning of PI3K. As disorders of immune system attributable to the hyperfunctioning of PI3K, mention may be made of: autoimmune diseases such as rheumatoid arthritis, systemic lupus erythematosus, scleroderma, Sjögren syndrome, or the like; organ dysfunction associated with autoimmune diseases such as uveitis, glomerulonephritis, thyroiditis, pancreatitis, bone destruction or the like; rejection after transplantation of tissues, graft versus host disease after bone-marrow transplantation; inflammatory bowel diseases such as ulcerative colitis or Crohn disease; inflammatory or allergenic skin diseases such as psoriasis or atopic dermatitis; inflammatory or allergenic respiratory disorders such as chronic obstructive pulmonary disease or asthma; allergenic conjunctivitis or rhinitis; hematologic neoplasm originated from immune cells, such as B-cell lymphoma, T-cell lymphoma, myeloid leukemia or the like; sepsis triggered by infection to gram-negative bacteria or coronavirus, severe acute respiratory syndrome, fulminant hepatitis or the like.

Assay Example 13

Test for Measuring Blood Level

A pharmacokinetic study was performed using 6 week-old BDF1 male mice. The test substances were mixed with hydroxylpropylcellulose (low-molecular weight form) [HPC (L)] in 2.5-fold of the drug weight, and dissolved in dichloromethane. The solvent was evaporated to dryness. To make the dosing formation, the residue was suspended in distilled water to prepare the drug level of 20 mg/mL. The test compounds were administered compulsorily and orally at a dose of 200 mg/kg to the mice that had been starved for 16 hours. One hour after the administration, blood was collected from the orbits of two mice to obtain serum. Internal standards solution and 1 ml of distilled water were added to 100 μL, of serum thus obtained, and then extracted with diethylether. The solvent was evaporated under vacuum, and the residue was resolved with eluent to provide samples for the HPLC measurement. HPLC was performed by using reversed-phase type column, and acetonitrile-phosphate buffer (pH 2.5) was used as the eluent. Using regression curves (Y=aX+b) obtained from the standards, the drug levels in the sample serum were calculated. Their results are shown in Table 7 below.

TABLE 7

| Test Compounds | Serum Level (μg/mL) |
| --- | --- |
| Compound 28 | 16.13 |
| Compound 36 | 7.17 |
| Compound 37 | 4.76 |
| Compound 38 | 5.91 |

As shown in the above test results, the compounds of the present invention having an acyl group at position 4 of the piperazine ring exhibited high blood levels quickly, one hour after the administration, as compared with the known control compounds 2, 3 and 9.

Assay Example 14

Proliferation Inhibitory Activity on Solid Tumor Cells

Used in the test were MCF-7 cells which were established from human breast cancer and were cultured routinely under the conditions of 37° C. and 5% $CO_2$, in MEM medium supplemented with 10% fetal calf serum, 25 mM of HEPES and 0.1 mg/ml kanamycin. The MCF-7 cells in a logarithmic growth phase were treated with trypsin/EDTA to prepare single cell suspension adjusted to $4.0 \times 10^4$ cells/ml in MEM medium (supplemented with 10% fetal calf serum, 25 mM of HEPES and 0.1 mg/ml kanamycin). Test compounds were dissolved in DMSO and diluted with RPMI 1640 medium (supplemented with 10% fetal calf serum, 25 mM of HEPES and 0.1 mg/ml kanamycin) to a concentration of $2.0 \times 10^4$ to $2.0 \times 10^{-9}$M.

The cell suspension was filled in a 96-wells microplate at a rate of 0.1 ml per well and was cultured for 24 hours so as to make the cells to adhere to the microplate. Then, it was added with 0.1 ml of the sample solution and cultured at 37° C. for 72 hours in 5% $CO_2$.

50% Growth inhibition concentrations ($GI_{50}$ μM) were calculated from growth inhibitions at various sample concentrations. The results are as shown in Table 8.

In the foregoing, when the cells other than MCF-7 are used, instead of adding 10% fetal bovine serum, the following media were used, and the following single cell suspensions were prepared.

PC-3 prostate cancer cells: 10% fetal bovine serum in F12K medium, single cell suspension of $2 \times 10^4$ cells;
A549 lung cancer cells: 10% fetal bovine serum in DMEM medium, single cell suspension of $1.5 \times 10^4$ cells;
WiDr colon cancer cells: 10% fetal bovine serum in MEM medium, single cell suspension of $3 \times 10^4$ cells;
B16F10 melanoma cells: 10% fetal bovine serum in RPMI 1640 medium, single cell suspension of $1 \times 10^4$ cells;

TABLE 8

|  | PC-3 | B16F10 | WiDr | A549 | $GI_{50}$ (μM) MCF-7 |
| --- | --- | --- | --- | --- | --- |
| Compound 25 | 0.27 | 3.21 | 0.92 | 0.99 | 0.98 |
| Compound 27 | 0.31 | 4.63 | 1.32 | 1.12 | 1.14 |
| Compound 28 | 0.27 | 2.66 | 1.27 | 0.83 | 1.21 |
| Compound 29 | 0.32 | 3.93 | 2.58 | 1.32 | 0.70 |
| Compound 30 | 0.77 | 3.32 | 3.74 | 1.52 | 0.41 |
| Compound 31 | 0.32 | 1.51 | 1.43 | 0.65 | 0.05 |
| Compound 32 | 0.38 | 2.14 | 1.33 | 0.83 | <0.04 |
| Compound 33 | 0.51 | 2.91 | 1.46 | 1.05 | <0.04 |
| Compound 34 | 0.55 | 2.91 | 2.07 | 1.38 | 0.14 |
| Compound 35 | 0.73 | 2.84 | 2.10 | 1.22 | 0.10 |

Industrial Applicability

The agents of the present invention can be used for the prevention or treatment of disorders of immune system involving in PI3K, such as autoimmune diseases, organ transplantation, allergic or inflammatory diseases, hematologic neoplasm, sepsis or the like. Furthermore, they can be used for the treatment of solid tumors. Moreover, they can be used as PI3K inhibitors for the treatment of a variety of disorders.

What is claimed is:

1. A heterocyclic compound represented by the general Formula (II):

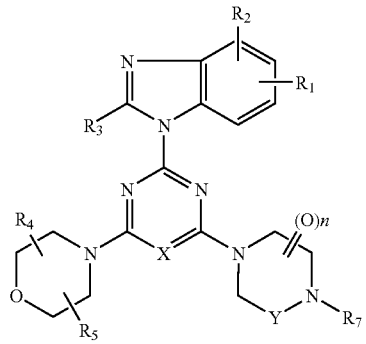

wherein,
n represents 0-2;
X represents a nitrogen atom or CH;
Y represents -$(CH_2)n_1$-, wherein $n_1$ is 1-2;
$R_1$ and $R_2$, both or either, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a difluoromethyl group, a $C_1$-$C_6$ alkylamino group or a hydroxymethyl group;
$R_4$ and $R_5$ represent a hydrogen, or a $C_1$-$C_6$ alkyl group;
$R_7$ represents a hydrogen atom, a $C_1$-$C_6$ alkyl group, a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, or a substituted carbamoyl;
or a pharmaceutically acceptable salt thereof.

2. The compound according to claim 1, wherein the heterocyclic compound is selected from the group consisting of: A heterocyclic compound selected form the group consisting of:
4-(4-acetylpiperazin-1-yl)-2-(2-difluoromethylbenzimidazol-1-yl)-6-morpholino-1,3,5-triazine;

4-(4-acetylpiperazin-1-yl)-2-(2-difluoromethylbenzimidazol-1-yl)-6-(cis-2,3-dimethylmorpholino)-1,3,5-triazine;
4-(4-acetylpiperazin-1-yl)-2-(2-difluoromethylbenzimidazol-1-yl)-6-(trans-2,3-dimethylmorpholino)-1,3,5-triazine;
4-(4-acetylpiperazin-1-yl)-2-(2-difluoromethylbenzimidazol-1-yl)-6-(2,2-dimethylmorpholino)-1,3,5-triazine;
4-(4-acetylpiperazin-1-yl)-2-(2-difluoromethyl-4-hydroxybenzimidazol-1-yl)-6-morpholino-1,3,5-triazine;
4-(4-acetylpiperazin-1-yl)-2-(4-amino-2-difluoromethylbenzimidazol-1-yl)-6-morpholino-1,3,5-triazine;
4-(4-acetylpiperazin-1-yl)-2-(2-hydroxymethylbenzimidazol-1-yl)-6-morpholino-1,3,5-triazine;
4-(4-acetylpiperazin-1-yl)-2-(2-difluoromethylbenzimidazol-1-yl)-6-morpholinopyrimidine;
4-(4-acetylpiperazin-1-yl)-2-(2-difluoromethylbenzimidazol-1-yl)-6-(cis-2,3-dimethylmorpholino)pyrimidine;
4-(4-acetylpiperazin-1-yl)-2-(2-difluoromethylbenzimidazol-1-yl)-6-(trans-2,3-dimethylmorpholino)pyrimidine;
4-(4-acetylpiperazin-1-yl)-2-(2-difluoromethylbenzimidazol-1-yl)-6-(2,2-dimethylmorpholino)pyrimidine;
4-(4-acetylpiperazin-1-yl)-2-(2-difluoromethyl-4-hydroxybenzimidazol-1-yl)-6-morpholinopyrimidine;
4-(4-acetylpiperazin-1-yl)-2-(4-amino-2-difluoromethylbenzimidazol-1-yl)-6-morpholinopyrimidine;
4-(4-acetylpiperazin-1-yl)-2-(2-hydroxymethylbenzimidazol-1-yl)-6-morpholinopyrimidine;
2-(2-difluoromethylbenzimidazol-1-yl)-4-[4-(N,N-dimethylcarbamoyl)piperazin-1-yl]-6-morpholino-1,3,5-triazine;
2-(2-difluoromethylbenzimidazol-1-yl)-4-[4-(N,N-dimethylcarbamoyl)piperazin-1-yl]-6-(cis-2,3-dimethylmorpholino)-1,3,5-triazine;
2-(2-difluoromethylbenzimidazol-1-yl)-4-[4-(N,N-dimethylcarbamoyl)piperazin-1-yl]-6-(trans-2,3-dimethylmorpholino)-1,3,5-triazine;
2-(2-difluoromethylbenzimidazol-1-yl)-4-[4-(N,N-dimethylcarbamoyl)piperazin-1-yl]-6-(2,2-dimethylmorpholino)-1,3,5-triazine;
2-(2-difluoromethyl-4-hydroxybenzimidazol-1-yl)-4-[4-(N,N-dimethylcarbamoyl)piperazin-1-yl]-6-morpholino-1,3,5-triazine;
2-(4-amino-2-difluoromethylbenzimidazol-1-yl)-4-[4-(N,N-dimethylcarbamoyl)piperazin-1-yl]-6-morpholino-1,3,5-triazine;
2-(2-hydroxymethylbenzimidazol-1-yl)-4-[4-(N,N-dimethylcarbamoyl)piperazin-1-yl]-6-morpholino-1,3,5-triazine;
2-(2-difluoromethylbenzimidazol-1-yl)-4-[4-(N,N-dimethylcarbamoyl)piperazin-1-yl]-6-morpholinopyrimidine;
2-(2-difluoromethylbenzimidazol-1-yl)-4-[4-(N,N-dimethylcarbamoyl)piperazin-1-yl]-6-(cis-2,3-dimethylmorpholino)pyrimidine;
2-(2-difluoromethylbenzimidazol-1-yl)-4-[4-(N,N-dimethylcarbamoyl)piperazin-1-yl]-6-(trans-2,3-dimethylmorpholino)pyrimidine;
2-(2-difluoromethylbenzimidazol-1-yl)-4-[4-(N,N-dimethylcarbamoyl)piperazin-1-yl]-6-(2,2-dimethylmorpholino)pyrimidine;
2-(2-difluoromethyl-4-hydroxybenzimidazol-1-yl)-4-[4-(N,N-dimethylcarbamoyl)piperazin-1-yl]-6-morpholinopyrimidine;
2-(4-amino-2-difluoromethylbenzimidazol-1-yl)-4-[4-(N,N-dimethylcarbamoyl)piperazin-1-yl]-6-morpholinopyrimidine;
2-(2-hydroxymethylbenzimidazol-1-yl)-4-[4-(N,N-dimethylcarbamoyl)piperazin-1-yl]-6-morpholinopyrimidine;
2-(2-difluoromethylbenzimidazol-1-yl)-4-[4-(2-furoyl)piperazin-1-yl]-6-morpholino-1,3,5-triazine;
2-(2-difluoromethylbenzimidazol-1-yl)-4-[4-(2-furoyl)piperazin-1-yl]-6-(cis-2,3-dimethylmorpholino)-1,3,5-triazine;
2-(2-difluoromethylbenzimidazol-1-yl)-4-[4-(2-furoyl)piperazin-1-yl]-6-(trans-2,3-dimethylmorpholino)-1,3,5-triazine;
2-(2-difluoromethylbenzimidazol-1-yl)-4-[4-(2-furoyl)piperazin-1-yl]-6-(2,2-dimethylmorpholino)-1,3,5-triazine;
2-(2-difluoromethyl-4-hydroxybenzimidazol-1-yl)-4-[4-(2-furoyl)piperazin-1-yl]-6-morpholino-1,3,5-triazine;
2-(4-amino-2-difluoromethylbenzimidazol-1-yl)-4-[4-(2-furoyl)piperazin-1-yl]-6-morpholino-1,3,5-triazine;
4-[4-(2-furoyl)piperazin-1-yl]-2-(2-hydroxymethylbenzimidazol-1-yl)-6-morpholino-1,3,5-triazine;
2-(2-difluoromethylbenzimidazol-1-yl)-4-[4-(2-furoyl)piperazin-1-yl]-6-morpholinopyrimidine;
2-(2-difluoromethylbenzimidazol-1-yl)-4-[4-(2-furoyl)piperazin-1-yl]-6-(cis-2,3-dimethylmorpholino)pyrimidine;
2-(2-difluoromethylbenzimidazol-1-yl)-4-[4-(2-furoyl)piperazin-1-yl]-6-(trans-2,3-dimethylmorpholino)pyrimidine;
2-(2-difluoromethylbenzimidazol-1-yl)-4-[4-(2-furoyl)piperazin-1-yl]-6-(2,2-dimethylmorpholino)pyrimidine;
2-(2-difluoromethyl-4-hydroxybenzimidazol-1-yl)-4-[4-(2-furoyl)piperazin-1-yl]-6-morpholinopyrimidine;
2-(4-amino-2-difluoromethylbenzimidazol-1-yl)-4-[4-(2-furoyl)piperazin-1-yl]-6-morpholinopyrimidine;
4-[4-(2-furoyl)piperazin-1-yl]-2-(2-hydroxymethylbenzimidazol-1-yl)-6-morpholinopyrimidine;
4-(4-acetonylpiperazin-1-yl)-2-(2-difluoromethylbenzimidazol-1-yl)-6-morpholino-1,3,5-triazine;
4-(4-acetonylpiperazin-1-yl)-2-(2-difluoromethylbenzimidazol-1-yl)-6-(cis-2,3-ditnethylmorpholino)-1,3,5-triazine;
4-(4-acetonylpiperazin-1-yl)-2-(2-difluoromethylbenzimidazol-1-yl)-6-(trans-2,3-dimethylmorpholino)-1,3,5-triazine;
4-(4-acetonylpiperazin-1-yl)-2-(2-difluoromethylbenzimidazol-1-yl)-6-(2,2-dimethylmorpholino)-1,3,5-triazine;
4-(4-acetonylpiperazin-1-yl)-2-(2-difluoromethyl-4-hydroxybenzimidazol-1-yl)-6-morpholino-1,3,5-triazine;
4-(4-acetonylpiperazin-1-yl)-2-(4-amino-2-difluoromethylbenzimidazol-1-yl)-6-morpholino-1,3,5-triazine;
4-(4-acetonylpiperazin-1-yl)-2-(2-hydroxymethylbenzimidazol-1-yl)-6-morpholino-1,3,5-triazine;
4-(4-acetonylpiperazin-1-yl)-2-(2-difluoromethylbenzimidazol-1-yl)-6-morpholinopyrimidine;
4-(4-acetonylpiperazin-1-yl)-2-(2-difluoromethylbenzimidazol-1-yl)-6-(cis-2,3-dimethylmorpholino)pyrimidine;
4-(4-acetonylpiperazin-1-yl)-2-(2-difluoromethylbenzimidazol-1-yl)-6-(trans-2,3-dimethylmorpholino)pyrimidine;

4-(4-acetonylpiperazin-1-yl)-2-(2-difluoromethylbenzimidazol-1-yl)-6-(2,2-dimethylmorpholino)pyrimidine;
4-(4-acetonylpiperazin-1-yl)-2-(2-difluoromethyl-4-hydroxybenzimidazol-1-yl)-6-morpholinopyrimidine;
4-(4-acetonylpiperazin-1-yl)-2-(4-amino-2-difluoromethylbenzimidazol-1-yl)-6-morpholinopyrimidine;
4-(4-acetonylpiperazin-1-yl)-2-(2-hydroxymethylbenzimidazol-1-yl)-6-morpholinopyrimidine;
2-(2-difluoromethylbenzimidazol-1-yl)-4-morpholino-6-(4-propionylpiperazin-1-yl)-1,3,5-triazine;
2-(2-difluoromethylbenzimidazol-1-yl)-4-(cis-2,3-dimethylmorpholino)-6-(4-propionylpiperazin-1-yl)-1,3,5-triazine;
2-(2-difluoromethylbenzimidazol-1-yl)-4-(trans-2,3-dimethylmorpholino)-6-(4-propionylpiperazin-1-yl)-1,3,5-triazine;
2-(2-difluoromethylbenzimidazol-1-yl)-4-(2,2-dimethylmorpholino)-6-(4-propionylpiperazin-1-yl)-1,3,5-triazine;
2-(2-difluoromethyl-4-hydroxybenzimidazol-1-yl)-4-morpholino-6-(4-propionylpiperazin-1-yl)-1,3,5-triazine;
2-(4-amino-2-difluoromethylbenzimidazol-1-yl)-4-morpholino-6-(4-propionylpiperazin-1-yl)-1,3,5-triazine;
2-(2-hydroxymethylbenzimidazol-1-yl)-4-morpholino-6-(4-propionylpiperazin-1-yl)-1,3,5-triazine;
2-(2-difluoromethylbenzimidazol-1-yl)-4-morpholino-6-(4-propionylpiperazin-1-yl)pyrimidine;
2-(2-difluoromethylbenzimidazol-1-yl)-4-(cis-2,3-dimethylmorpholino)-6-(4-propionylpiperazin-1-yl)pyrimidine;
2-(2-difluoromethylbenzimidazol-1-yl)-4-(trans-2,3-dimethylmorpholino)-6-(4-propionylpiperazin-1-yl)pyrimidine;
2-(2-difluoromethylbenzimidazol-1-yl)-4-(2,2-dimethylmorpholino)-6-(4-propionylpiperazin-1-yl)pyrimidine;
2-(2-difluoromethyl-4-hydroxybenzimidazol-1-yl)-4-morpholino-6-(4-propionylpiperazin-1-yl)pyrimidine;
2-(4-amino-2-difluoromethylbenzimidazol-1-yl)-4-morpholino-6-(4-propionylpiperazin-1-yl)pyrimidine;
2-(2-hydroxymethylbenzimidazol-1-yl)-4-morpholino-6-(4-propionylpiperazin-1-yl)pyrimidine;
2-(2-difluoromethylbenzimidazol-1-yl)-4-(4-methoxyacetylpiperazin-1-yl)-6-morpholino-1,3,5-triazine;
2-(2-difluoromethylbenzimidazol-1-yl)-4-(4-methoxyacetylpiperazin-1-yl)-6-(cis-2,3-dimethylmorpholino)-1,3,5-triazine;
2-(2-difluoromethylbenzimidazol-1-yl)-4-(4-methoxyacetylpiperazin-1-yl)-6-(trans-2,3-dimethylmorpholino)-1,3,5-triazine;
2-(2-difluoromethylbenzimidazol-1-yl)-4-(4-methoxyacetylpiperazin-1-yl)-6-(2,2-dimethylmorpholino)-1,3,5-triazine;
2-(2-difluoromethyl-4-hydroxybenzimidazol-1-yl)-4-(4-methoxyacetylpiperazin-1-yl)-6-morpholino-1,3,5-triazine;
2-(4-amino-2-difluoromethylbenzimidazol-1-yl)-4-(4-methoxyacetylpiperazin-1-yl)-6-morpholino-1,3,5-triazine;
2-(2-hydroxymethylbenzimidazol-1-yl)-4-(4-methoxyacetylpiperazin-1-yl)-6-morpholino-1,3,5-triazine;
2-(2-difluoromethylbenzimidazol-1-yl)-4-(4-methoxyacetylpiperazin-1-yl)-6-morpholinopyrimidine;
2-(2-difluoromethylbenzimidazol-1-yl)-4-(4-methoxyacetylpiperazin-1-yl)-6-(cis-2,3-dimethylmorpholino)pyrimidine;
2-(2-difluoromethylbenzimidazol-1-yl)-4-(4-methoxyacetylpiperazin-1-yl)-6-(trans-2,3-dimethylmorpholino)pyrimidine;
2-(2-difluoromethylbenzimidazol-1-yl)-4-(4-methoxyacetylpiperazin-1-yl)-6-(2,2-dimethylmorpholino)pyrimidine;
2-(2-difluoromethyl-4-hydroxybenzimidazol-1-yl)-4-(4-methoxyacetylpiperazin-1-yl)-6-morpholinopyrimidine;
2-(4-amino-2-difluoromethylbenzimidazol-1-yl)-4-(4-methoxyacetylpiperazin-1-yl)-6-morpholinopyrimidine;
2-(2-hydroxymethylbenzimidazol-1-yl)-4-(4-methoxyacetylpiperazin-1-yl)-6-morpholinopyrimidine;
2-(2-difluoromethylbenzimidazol-1-yl)-4-[4-(3-hydroxypropyl)piperazin-1-yl]-6-morpholino-1,3,5-triazine;
2-(2-difluoromethylbenzimidazol-1-yl)-4-[4-(3-hydroxypropyppiperazin-1-yl]-6-(cis-2,3-dimethylmorpholino)-1,3,5-triazine;
2-(2-difluoromethylbenzimidazol-1-yl)-4-[4-(3-hydroxypropyl)piperazin-1-yl]-6-(trans-2,3-dimethylmorpholino)-1,3,5-triazine;
2-(2-difluoromethylbenzimidazol-1-yl)-4-[4-(3-hydroxypropyl)piperazin-1-yl]-6-(2,2-dimethylmorpholino)-1,3,5-triazine;
2-(2-difluoromethyl-4-hydroxybenzimidazol-1-yl)-4-[4-(3-hydroxypropyl)piperazin-1-yl]-6-morpholino-1,3,5-triazine;
2-(4-amino-2-difluoromethylbenzimidazol-1-yl)-4-[4-(3-hydroxypropyl)piperazin-1-yl]-6-morpholino-1,3,5-triazine;
2-(2-hydroxymethylbenzimidazol-1-yl)-4-[4-(3-hydroxypropyl)piperazin-1-yl]-6-morpholino-1,3,5-triazine;
2-(2-difluoromethylbenzimidazol-1-yl)-4-[4-(3-hydroxypropyl)piperazin-1-yl]-6-morpholinopyrimidine;
2-(2-difluoromethylbenzimidazol-1-yl)-4-[4-(3-hydroxypropyl)piperazin-1-yl]-6-(cis-2,3-dimethylmorpholino)pyrimidine;
2-(2-difluoromethylbenzimidazol-1-yl)-4-[4-(3-hydroxypropyl)piperazin-1-yl]-6-(trans-2,3-dimethylmorpholino)pyrimidine;
2-(2-difluoromethylbenzimidazol-1-yl)-4-[4-(3-hydroxypropyl)piperazin-1-yl]-6-(2,2-dimethylmorpholino)pyrimidine;
2-(2-difluoromethyl-4-hydroxybenzimidazol-1-yl)-4-[4-(3-hydroxypropyl)piperazin-1-yl]-6-morpholinopyrimidine;
2-(4-amino-2-difluoromethylbenzimidazol-1-yl)-4-[4-(3-hydroxypropyl)piperazin-1-yl]-6-morpholinopyrimidine;
2-(2-hydroxymethylbenzimidazol-1-yl)-4-[4-(3-hydroxypropyl)piperazin-1-yl]-6-morpholinopyrimidine;
2-(2-difluoromethylbenzimidazol-1-yl)-4-(4-methoxycarbonylpiperazin-1-yl)-6-morpholino-1,3,5-triazine;
2-(2-difluoromethylbenzimidazol-1-yl)-4-(4-methoxycarbonylpiperazin-1-yl)-6-(cis-2,3-dimethylmorpholino)-1,3,5-triazine;
2-(2-difluoromethylbenzimidazol-1-yl)-4-(4-methoxycarbonylpiperazin-1-yl)-6-(trans-2,3-dimethylmorpholino)-1,3,5-triazine;
2-(2-difluoromethylbenzimidazol-1-yl)-4-(4-methoxycarbonylpiperazin-1-yl)-6-(2,2-dimethylmorpholino)-1,3,5-triazine;
2-(2-difluoromethyl-4-hydroxybenzimidazol-1-yl)-4-(4-methoxycarbonylpiperazin-1-yl)-6-morpholino-1,3,5-triazine;

2-(4-amino-2-difluoromethylbenzimidazol-1-yl)-4-(4-methoxycarbonylpiperazin-1-yl)-6-morpholino-1,3,5-triazine;

2-(2-hydroxymethylbenzimidazol-1-yl)-4-(4-methoxycarbonylpiperazin-1-yl)-6-morpholino-1,3,5-triazine;

2-(2-difluoromethylbenzimidazol-1-yl)-4-(4-methoxycarbonylpiperazin-1-yl)-6-morpholinopyrimidine;

2-(2-difluoromethylbenzimidazol-1-yl)-4-(4-methoxycarbonylpiperazin-1-yl)-6-(cis-2,3-dimethylmorpholino)pyrimidine;

2-(2-difluoromethylbenzimidazol-1-yl)-4-(4-methoxycarbonylpiperazin-1-yl)-6-(trans-2,3-dimethylmorpholino)pyrimidine;

2-(2-difluoromethylbenzimidazol-1-yl)-4-(4-methoxycarbonylpiperazin-1-yl)-6-(2,2-dimethylmorpholino)pyrimidine;

2-(2-difluoromethyl-4-hydroxybenzimidazol-1-yl)-4-(4-methoxycarbonylpiperazin-1-yl)-6-morpholinopyrimidine;

2-(4-amino-2-difluoromethylbenzimidazol-1-yl)-4-(4-methoxycarbonylpiperazin-1-yl)-6-morpholinopyrimidine;

2-(2-hydroxymethylbenzimidazol-1-yl)-4-(4-methoxycarbonylpiperazin-1-yl)-6-morpholinopyrimidine;

2-(2-difluoromethylbenzimidazol-1-yl)-4-morpholino-6-(5-oxo-1,4-diazepan-1-yl)-1,3,5-triazine;

2-(2-difluoromethylbenzimidazol-1-yl)-4-morpholino-6-(3-oxopiperazin-1-yl)-1,3,5-triazine; and 2-(2-difluoromethylbenzimidazol-1-yl)-6-(3,5-dioxopiperazin-1-yl)-4-morpholino-1,3,5-triazine.

3. A method for immunosuppression in a mammal suffering from an immune disease, comprising administering to the mammal a therapeutically effective amount of the heterocyclic compound according to claim 1 or a pharmaceutically acceptable salt thereof wherein said immune disease is atopic dermatitis or rheumatoid arthritis.

4. The method according to claim 1, wherein either of $R_1$ or $R_2$ is a hydroxyl group.

5. The method according to claim 1, wherein either of $R_1$ or $R_2$ is a hydroxyl group, and $R_3$ is a difluoromethyl.

6. The method according to claim 1, wherein both of $R_1$ and $R_2$ are hydrogens, and $R_3$ is a difluoromethyl.

7. The method according to claim 1, wherein $n_1$ is 1, n is 0, and $R_7$ is acetyl.

8. The method according to claim 1, wherein the heterocyclic compound is selected from the group consisting of:
4-(4-acetylpiperazin-1-yl)-2-(2-difluoromethylbenzimidazol-1-yl)-6-morpholinopyrimidine; and
4-(4-acetylpiperazin-1-yl)-2-(2-difluoromethylbenzimidazol-1-yl)-6-morpholino-1,3,5-triazine.

9. The method according to claim 1, wherein said immune disease is an atopic dermatitis.

10. The method according to claim 1, wherein said immune disease is an rheumatoid arthritis.

11. A method for immunosuppression in a mammal suffering from an immune disease, comprising administering to the mammal a therapeutically effective amount of a heterocyclic compound, wherein said immune disease is atopic dermatitis or rheumatoid arthritis and the heterocyclic compound is selected form the group consisting of:
4-(4-acetylpiperazin-1-yl)-2-(2-difluoromethylbenzimidazol-1-yl)-6-morpholino-1,3,5-triazine;
4-(4-acetylpiperazin-1-yl)-2-(2-difluoromethylbenzimidazol-1-yl)-6-(cis-2,3-dimethylmorpholino)-1,3,5-triazine;
4-(4-acetylpiperazin-1-yl)-2-(2-difluoromethylbenzimidazol-1-yl)-6-(trans-2,3-dimethylmorpholino)-1,3,5-triazine;
4-(4-acetylpiperazin-1-yl)-2-(2-difluoromethylbenzimidazol-1-yl)-6-(2,2-dimethylmorpholino)-1,3,5-triazine;
4-(4-acetylpiperazin-1-yl)-2-(2-difluoromethyl-4-hydroxybenzimidazol-1-yl)-6-morpholino-1,3,5-triazine;
4-(4-acetylpiperazin-1-yl)-2-(4-amino-2-difluoromethylbenzimidazol-1-yl)-6-morpholino-1,3,5-triazine;
4-(4-acetylpiperazin-1-yl)-2-(2-hydroxymethylbenzimidazol-1-yl)-6-morpholino-1,3,5-triazine;
4-(4-acetylpiperazin-1-yl)-2-(2-difluoromethylbenzimidazol-1-yl)-6-morpholinopyrimidine;
4-(4-acetylpiperazin-1-yl)-2-(2-difluoromethylbenzimidazol-1-yl)-6-(cis-2,3-dimethylmorpholino)pyrimidine;
4-(4-acetylpiperazin-1-yl)-2-(2-difluoromethylbenzimidazol-1-yl)-6-(trans-2,3-dimethylmorpholino)pyrimidine;
4-(4-acetylpiperazin-1-yl)-2-(2-difluoromethylbenzimidazol-1-yl)-6-(2,2-dimethylmorpholino)pyrimidine;
4-(4-acetylpiperazin-1-yl)-2-(2-difluoromethyl-4-hydroxybenzimidazol-1-yl)-6-morpholinopyrimidine;
4-(4-acetylpiperazin-1-yl)-2-(4-amino-2-difluoromethylbenzimidazol-1-yl)-6-morpholinopyrimidine;
4-(4-acetylpiperazin-1-yl)-2-(2-hydroxymethylbenzimidazol-1-yl)-6-morpholinopyrimidine;
2-(2-difluoromethylbenzimidazol-1-yl)-4-[4-(N,N-dimethylcarbamoyl)piperazin-1-yl]-6-morpholino-1,3,5-triazine;
2-(2-difluoromethylbenzimidazol-1-yl)-4-[4-(N,N-dimethylcarbamoyl)piperazin-1-yl]-6-(cis-2,3-dimethylmorpholino)-1,3,5-triazine;
2-(2-difluoromethylbenzimidazol-1-yl)-4-[4-(N,N-dimethylcarbamoyl)piperazin-1-yl]-6-(trans-2,3-dimethylmorpholino)-1,3,5-triazine;
2-(2-difluoromethylbenzimidazol-1-yl)-4-[4-(N,N-dimethylcarbamoyl)piperazin-1-yl]-6-(2,2-dimethylmorpholino)-1,3,5-triazine;
2-(2-difluoromethyl-4-hydroxybenzimidazol-1-yl)-4-[4-(N,N-dimethylcarbamoyl)piperazin-1-yl]-6-morpholino-1,3,5-triazine;
2-(4-amino-2-difluoromethylbenzimidazol-1-yl)-4-[4-(N,N-dimethylcarbamoyl)piperazin-1-yl]-6-morpholino-1,3,5-triazine;
2-(2-hydroxymethylbenzimidazol-1-yl)-4[4-(N,N-dimethylcarbamoyl)piperazin-1-yl]-6-morpholino-1,3,5-triazine;
2-(2-difluoromethylbenzimidazol-1-yl)-4-[4-(N,N-dimethylcarbamoyl)piperazin-1-yl]-6-morpholinopyrimidine;
2-(2-difluoromethylbenzimidazol-1-yl)-4-[4-(N,N-dimethylcarbamoyl)piperazin-1-yl]-6-(cis-2,3-dimethylmorpholino)pyrimidine;
2-(2-difluoromethylbenzimidazol-1-yl)-4-[4-(N,N-dimethylcarbamoyl)piperazin-1-yl]-6-(trans-2,3-dimethylmorpholino)pyrimidine;
2-(2-difluoromethylbenzimidazol-1-yl)-4-[4-(N,N-dimethylcarbamoyl)piperazin-1-yl]-6-(2,2-dimethylmorpholino)pyrimidine;
2-(2-difluoromethyl-4-hydroxybenzimidazol-1-yl)-4-[4-(N,N-dimethylcarbamoyl)piperazin-1-yl]-6-morpholinopyrimidine;
2-(4-amino-2-difluoromethylbenzimidazol-1-yl)-4-[4-(N,N-dimethylcarbamoyl)piperazin-1-yl]-6-morpholinopyrimidine;

2-(2-hydroxymethylbenzimidazol-1-yl)-4[4-(N,N-dimethylcarbamoyl)piperazin-1-yl]-6-morpholinopyrimidine;
2-(2-difluoromethylbenzimidazol-1-yl)-4-[4-(2-furoyl)piperazin-1-yl]-6-morpholino-1,3,5-triazine;
2-(2-difluoromethylbenzimidazol-1-yl)-4-[4-(2-furoyl)piperazin-1-yl]-6-(cis-2,3-dimethylmorpholino)-1,3,5-triazine;
2-(2-difluoromethylbenzimidazol-1-yl)-4-[4-(2-furoyl)piperazin-1-yl]-6-(trans-2,3-dimethylmorpholino)-1,3,5-triazine;
2-(2-difluoromethylbenzimidazol-1-yl)-4-[4-(2-furoyl)piperazin-1-yl]-6-(2,2-dimethylmorpholino)-1,3,5-triazine;
2-(2-difluoromethyl-4-hydroxybenzimidazol-1-yl)-4-[4-(2-furoyl)piperazin-1-yl]-6-morpholino-1,3,5-triazine;
2-(4-amino-2-difluoromethylbenzimidazol-1-yl)-4-[4-(2-furoyl)piperazin-1-yl]-6-morpholino-1,3,5-triazine;
4-[4-(2-furoyl)piperazin-1-yl]-2-(2-hydroxymethylbenzimidazol-1-yl)-morpholino-1,3,5-triazine;
2-(2-difluoromethylbenzimidazol-1-yl)-4-[4-(2-furoyl)piperazin-1-yl]-6-morpholinopyrimidine;
2-(2-difluoromethylbenzimidazol-1-yl)-4-[4-(2-furoyl)piperazin-1-yl]-6-(cis-2,3-dimethylmorpholino)pyrimidine;
2-(2-difluoromethylbenzimidazol-1-yl)-4-[4-(2-furoyl)piperazin-1-yl]-6-(trans-2,3-dimethylmorpholino)pyrimidine;
2-(2-difluoromethylbenzimidazol-1-yl)-4-[4-(2-furoyl)piperazin-1-yl]-6-(2,2-dimethylmorpholino)pyrimidine;
2-(2-difluoromethyl-4-hydroxybenzimidazol-1-yl)-4-[4-(2-furoyl)piperazin-1-yl]-6-morpholinopyrimidine;
2-(4-amino-2-difluoromethylbenzimidazol-1-yl)-4-[4-(2-furoyl)piperazin-1-yl]-6-morpholinopyrimidine;
4-[4-(2-furoyl)piperazin-1-yl]-2-(2-hydroxymethylbenzimidazol-1-yl)-6-morpholinopyrimidine;
4-(4-acetonylpiperazin-1-yl)-2-(2-difluoromethylbenzimidazol-1-yl)-6-morpholino-1,3,5-triazine;
4-(4-acetonylpiperazin-1-yl)-2-(2-difluoromethylbenzimidazol-1-yl)-6-(cis-2,3-dimethylmorpholino)-1,3,5-triazine;
4-(4-acetonylpiperazin-1-yl)-2-(2-difluoromethylbenzimidazol-1-yl)-6-(trans-2,3-dimethylmorpholino)-1,3,5-triazine;
4-(4-acetonylpiperazin-1-yl)-2-(2-difluoromethylbenzimidazol-1-yl)-6-(2,2-dimethylmorpholino)-1,3,5-triazine;
4-(4-acetonylpiperazin-1-yl)-2-(2-difluoromethyl-4-hydroxybenzimidazol-1-yl)-6-morpholino-1,3,5-triazine;
4-(4-acetonylpiperazin-1-yl)-2-(4-amino-2-difluoromethylbenzimidazol-1-yl)-6-morpholino-1,3,5-triazine;
4-(4-acetonylpiperazin-1-yl)-2-(2-hydroxymethylbenzimidazol-1-yl)-6-morpholino-1,3,5-triazine;
4-(4-acetonylpiperazin-1-yl)-2-(2-difluoromethylbenzimidazol-1-yl)-6-morpholinopyrimidine;
4-(4-acetonylpiperazin-1-yl)-2-(2-difluoromethylbenzimidazol-1-yl)-6-(cis-2,3-dimethylmorpholino)pyrimidine;
4-(4-acetonylpiperazin-1-yl)-2-(2-difluoromethylbenzimidazol-1-yl)-6-(trans-2,3-dimethylmorpholino)pyrimidine;
4-(4-acetonylpiperazin-1-yl)-2-(2-difluoromethylbenzimidazol-1-yl)-6-(2,2-dimethylmorpholino)pyrimidine;
4-(4-acetonylpiperazin-1-yl)-2-(2-difluoromethyl-4-hydroxybenzimidazol-1-yl)-6-morpholinopyrimidine;
4-(4-acetonylpiperazin-1-yl)-2-(4-amino-2-difluoromethylbenzimidazol-1-yl)-6-morpholinopyrimidine;
4-(4-acetonylpiperazin-1-yl)-2-(2-hydroxymethylbenzimidazol-1-yl)-6-morpholinopyrimidine;
2-(2-difluoromethylbenzimidazol-1-yl)-4-morpholino-6-(4-propionylpiperazin-1-yl)-1,3,5-triazine;
2-(2-difluoromethylbenzimidazol-1-yl)-4-(cis-2,3-dimethylmorpholino)-6-(4-propionylpiperazin-1-yl)-1,3,5-triazine;
2-(2-difluoromethylbenzimidazol-1-yl)-4-(trans-2,3-dimethylmorpholino)-6-(4-propionylpiperazin-1-yl)-1,3,5-triazine;
2-(2-difluoromethylbenzimidazol-1-yl)-4-(2,2-dimethylmorpholino)-6-(4-propionylpiperazin-1-yl)-1,3,5-triazine;
2-(2-difluoromethyl-4-hydroxybenzimidazol-1-yl)-4-morpholino-6-(4-propionylpiperazin-1-yl)-1,3,5-triazine;
2-(4-amino-2-difluoromethylbenzimidazol-1-yl)-4-morpholino-6-(4-propionylpiperazin-1-yl)-1,3,5-triazine;
2-(2-hydroxymethylbenzimidazol-1-yl)-4-morpholino-6-(4-propionylpiperazin-1-yl)-1,3,5-triazine;
2-(2-difluoromethylbenzimidazol-1-yl)-4-morpholino-6-(4-propionylpiperazin-1-yl)pyrimidine;
2-(2-difluoromethylbenzimidazol-1-yl)-4-(cis-2,3-dimethylmorpholino)-6-(4-propionylpiperazin-1-yl)pyrimidine;
2-(2-difluoromethylbenzimidazol-1-yl)-4-(trans-2,3-dimethylmorpholino)-6-(4-propionylpiperazin-1-yl)pyrimidine;
2-(2-difluoromethylbenzimidazol-1-yl)-4-(2,2-dimethylmorpholino)-6-(4-propionylpiperazin-1-yl)pyrimidine;
2-(2-difluoromethyl-4-hydroxybenzimidazol-1-yl)-4-morpholino-6-(4-propionylpiperazin-1-yl)pyrimidine;
2-(4-amino-2-difluoromethylbenzimidazol-1-yl)-4-morpholino-6-(4-propionylpiperazin-1-yl)pyrimidine;
2-(2-hydroxymethylbenzimidazol-1-yl)-4-morpholino-6-(4-propionylpiperazin-1-yl)pyrimidine;
2-(2-difluoromethylbenzimidazol-1-yl)-4-(4-methoxyacetylpiperazin-1-yl)-6-morpholino-1,3,5-triazine;
2-(2-difluoromethylbenzimidazol-1-yl)-4-(4-methoxyacetylpiperazin-1-yl)-6-(cis-2,3-dimethylmorpholino)-1,3,5-triazine;
2-(2-difluoromethylbenzimidazol-1-yl)-4-(4-methoxyacetylpiperazin-1-yl)-6-(trans-2,3-dimethylmorpholino)-1,3,5-triazine;
2-(2-difluoromethylbenzimidazol-1-yl)-4-(4-methoxyacetylpiperazin-1-yl)-6-(2,2-dimethylmorpholino)-1,3,5-triazine;
2-(2-difluoromethyl-4-hydroxybenzimidazol-1-yl)-4-(4-methoxyacetylpiperazin-1-yl)-6-morpholino-1,3,5-triazine;
2-(4-amino-2-difluoromethylbenzimidazol-1-yl)-4-(4-methoxyacetylpiperazin-1-yl)-6-morpholino-1,3,5-triazine;
2-(2-hydroxymethylbenzimidazol-1-yl)-4-(4-methoxyacetylpiperazin-1-yl)-6-morpholino-1,3,5-triazine;
2-(2-difluoromethylbenzimidazol-1-yl)-4-(4-methoxyacetylpiperazin-1-yl)-6-morpholinopyrimidine;
2-(2-difluoromethylbenzimidazol-1-yl)-4-(4-methoxyacetylpiperazin-1-yl)-6-(cis-2,3-dimethylmorpholino)pyrimidine;
2-(2-difluoromethylbenzimidazol-1-yl)-4-(4-methoxyacetylpiperazin-1-yl)-6-(trans-2,3-dimethylmorpholino)pyrimidine;

2-(2-difluoromethylbenzimidazol-1-yl)-4-(4-methoxy-acetylpiperazin-1-yl)-6-(2,2-dimethylmorpholino)pyrimidine;
2-(2-difluoromethyl-4-hydroxybenzimidazol-1-yl)-4-(4-methoxyacetylpiperazin-1-yl)-6-morphohnopyrimidine;
2-(4-amino-2-difluoromethylbenzimidazol-1-yl)-4-(4-methoxyacetylpiperazin-1-yl)-6-morpholinopyrimidine;
2-(2-hydroxymethylbenzimidazol-1-yl)-4-(4-methoxyacetylpiperazin-1-yl)-6-morpholinopyrimidine;
2-(2-difluoromethylbenzimidazol-1-yl)-4-[4-(3-hydroxypropyl)piperazin-1-yl]-6-morpholino-1,3,5-triazine;
2-(2-difluoromethylbenzimidazol-1-yl)-4-[4-(3-hydroxypropyl)piperazin-1-yl]-6-(cis-2,3-dimethylmorpholino)-1,3,5-triazine;
2-(2-difluoromethylbenzimidazol-1-yl)-4-[4-(3-hydroxypropyl)piperazin-1-yl]-6-(trans-2,3-dimethylmorpholino)-1,3,5-triazine;
2-(2-difluoromethylbenzimidazol-1-yl)-4-[4-(3-hydroxypropyl)piperazin-1-yl]-6-(2,2-dimethylmorpholino)-1,3,5-triazine;
2-(2-difluoromethyl-4-hydroxybenzimidazol-1-yl)-4-[4-(3-hydroxypropyl)piperazin-1-yl]-6-morpholino-1,3,5-triazine;
2-(4-amino-2-difluoromethylbenzimidazol-1-yl)-4-[4-(3-hydroxypropyl)piperazin-1-yl]-6-morpholino-1,3,5-triazine;
2-(2-hydroxymethylbenzimidazol-1-yl)-4-[4-(3-hydroxypropyl)piperazin-1-yl]-6-morpholino-1,3,5-triazine;
2-(2-difluoromethylbenzimidazol-1-yl)-4-[4-(3-hydroxypropyl)piperazin-1-yl]-6-morpholinopyrimidine;
2-(2-difluoromethylbenzimidazol-1-yl)-4-[4-(3-hydroxypropyl)piperazin-1-yl]-6-(cis-2,3-dimethylmorpholino)pyrimidine;
2-(2-difluoromethylbenzimidazol-1-yl)-4-[4-(3-hydroxypropyl)piperazin-1-yl]-6-(trans-2,3-dimethylmorpholino)pyrimidine;
2-(2-difluoromethylbenzimidazol-1-yl)-4-[4-(3-hydroxypropyl)piperazin-1-yl]-6-(2,2-dimethylmorpholino)pyrimidine;
2-(2-difluoromethyl-4-hydroxybenzimidazol-1-yl)-4-[4-(3-hydroxypropyl)piperazin-1-yl]-6-morpholinopyrimidine;
2-(4-amino-2-difluoromethylbenzimidazol-1-yl)-4-[4-(3-hydroxypropyl)piperazin-1-yl]-6-morpholinopyrimidine;
2-(2-hydroxymethylbenzimidazol-1-yl)-4-[4-(3-hydroxypropyl)piperazin-1-yl]-6-morpholinopyrimidine;
2-(2-difluoromethylbenzimidazol-1-yl)-4-(4-methoxycarbonylpiperazin-1-yl)-6-morpholino-1,3,5-triazine;
2-(2-difluoromethylbenzimidazol-1-yl)-4-(4-methoxycarbonylpiperazin-1-yl)-6-(cis-2,3-dimethylmorpholino)-1,3,5-triazine;
2-(2-difluoromethylbenzimidazol-1-yl)-4-(4-methoxycarbonylpiperazin-1-yl)-6-(trans-2,3-dimethylmorpholino)-1,3,5-triazine;
2-(2-difluoromethylbenzimidazol-1-yl)-4-(4-methoxycarbonylpiperazin-1-yl)-6-(2,2-dimethylmorpholino)-1,3,5-triazine;
2-(2-difluoromethyl-4-hydroxybenzimidazol-1-yl)-4-(4-methoxycarbonylpiperazin-1-yl)-6-morpholino-1,3,5-triazine;
2-(4-amino-2-difluoromethylbenzimidazol-1-yl)-4-(4-methoxycarbonylpiperazin-1-yl)-6-morpholino-1,3,5-triazine;
2-(2-hydroxymethylbenzimidazol-1-yl)-4-(4-methoxycarbonylpiperazin-1-yl)-6-morpholino-1,3,5-triazine;
2-(2-difluoromethylbenzimidazol-1-yl)-4-(4-methoxycarbonylpiperazin-1-yl)-6-morpholinopyrimidine;
2-(2-difluoromethylbenzimidazol-1-yl)-4-(4-methoxycarbonylpiperazin-1-yl)-6-(cis-2,3-dimethylmorpholino)pyrimidine;
2-(2-difluoromethylbenzimidazol-1-yl)-4-(4-methoxycarbonylpiperazin-1-yl)-6-(trans-2,3-dimethylmorpholino)pyrimidine;
2-(2-difluoromethylbenzimidazol-1-yl)-4-(4-methoxycarbonylpiperazin-1-yl)-6-(2,2-dimethylmorpholino)pyrimidine;
2-(2-difluoromethyl-4-hydroxybenzimidazol-1-yl)-4-(4-methoxycarbonylpiperazin-1-yl)-6-morpholinopyrimidine;
2-(4amino-2-difluoromethylbenzimidazol-1-yl)-4-(4-methoxycarbonylpiperazin-1-yl)-6-morpholinopyrimidine;
2-(2-hydroxymethylbenzimidazol-1-yl)-4-(4-methoxycarbonylpiperazin-1-yl)-6-morpholinopyrimidine;
2-(2-difluoromethylbenzimidazol-1-yl)-4-morpholino-6-(5-oxo-1,4-diazepan-1-yl)-1,3,5-triazine;
2-(2-difluoromethylbenzimidazol-1-yl)-4-morpholino-6-(3-oxopiperazin-1-yl)-1,3,5-triazine; and
2-(2-difluoromethylbenzimidazol-1-yl)-6-(3,5-dioxopiperazin-1-yl)-4-morpholino-1,3,5-triazine.

12. A method for treating a tumor in a patient, comprising administering to the patient a therapeutically effective amount of a heterocyclic compound represented by the general Formula (II):

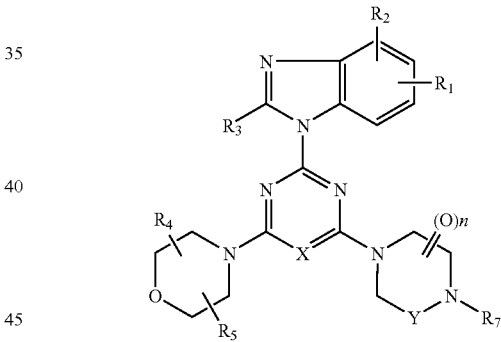

wherein,
n represents 0-2;
X represents a nitrogen atom or CH;
Y represents —$(CH_2)n_1$-, wherein $n_1$ is 1-2;
$R_1$ and $R_2$, both or either, represent a hydrogen atom, a hydroxyl group, a halogen, an amino group, a $C_1$-$C_6$ alkylamino group, a $C_1$-$C_6$ alkoxy group, a $C_1$-$C_6$ alkyl group, or a cyano group;
$R_3$ represents a difluoromethyl group, a $C_1$-$C_6$ alkylamino group or a hydroxymethyl group;
$R_4$ and $R_5$ represent a hydrogen, or a $C_1$-$C_6$ alkyl group;
$R_7$ represents a hydrogen atom, a $C_1$-$C_6$ alkyl group, a formyl, a $C_1$-$C_6$ hydroxyalkyl, a $C_1$-$C_6$ alkoxycarbonyl, a $C_1$-$C_6$ oxoalkyl, an aromatic carbonyl, a benzylcarbonyl, or a substituted carbamoyl;
or a pharmaceutically acceptable salt thereof wherein said cancer is selected from the group consisting of lung cancer, prostate cancer, breast cancer and colon cancer.

* * * * *